US008703910B2

(12) United States Patent
Tedford et al.

(10) Patent No.: US 8,703,910 B2
(45) Date of Patent: Apr. 22, 2014

(54) PEPTIDE TOXIN FORMULATION

(71) Applicant: Vestaron Corporation, Kalamazoo, MI (US)

(72) Inventors: William Tedford, Baton Rouge, LA (US); John McIntyre, Alto, MI (US); Daniel Russell, St. Louis, MO (US); Peter Carlson, Potomac, MD (US)

(73) Assignee: Vestaron Corproation, Kalamazoo, MI (US)

( * ) Notice: Subject to any disclaimer, the term of this patent is extended or adjusted under 35 U.S.C. 154(b) by 0 days.

(21) Appl. No.: 13/768,984

(22) Filed: Feb. 15, 2013

(65) Prior Publication Data

US 2013/0184434 A1    Jul. 18, 2013

Related U.S. Application Data

(60) Continuation of application No. 13/528,402, filed on Jun. 20, 2012, now Pat. No. 8,501,684, which is a division of application No. 12/568,400, filed on Sep. 28, 2009, now Pat. No. 8,217,003.

(60) Provisional application No. 61/101,825, filed on Oct. 1, 2008.

(51) Int. Cl.
    *C07K 14/435*    (2006.01)

(52) U.S. Cl.
    USPC ............................................. 530/324; 514/21.3

(58) Field of Classification Search
    USPC ........................................... 530/324; 514/21.3
    See application file for complete search history.

(56) References Cited

U.S. PATENT DOCUMENTS

| 4,337,194 | A | 6/1982 | Diaz et al. |
| 4,530,784 | A | 7/1985 | Rosenberg |
| 5,187,091 | A | 2/1993 | Donovan et al. |
| 5,591,443 | A | 1/1997 | Heinicke |
| 5,763,568 | A | 6/1998 | Atkinson et al. |
| 5,840,838 | A | 11/1998 | Hensley et al. |
| 6,583,264 | B2 | 6/2003 | King et al. |
| 7,173,106 | B2 | 2/2007 | King et al. |
| 7,279,547 | B2 | 10/2007 | King et al. |
| 7,354,993 | B2 * | 4/2008 | King et al. ............... 530/300 |
| 2007/0066529 | A1 * | 3/2007 | King et al. ............... 514/12 |

FOREIGN PATENT DOCUMENTS

| EP | 1812464 B1 | 6/2003 |
| WO | WO9315108 A1 | 8/1993 |
| WO | WO9618302 A1 | 6/1996 |
| WO | WO2006052806 A2 | 5/2006 |

OTHER PUBLICATIONS

Principles of Dairy Chemistry Jenness and Patton (1959) pp. 115-117, 127, 317, 326-328, 333.
de Dianous, S. et al., The effect of the mode of Application on the Toxicity of Androctonus Australis Hector Insect Toxin, Pesticide Science, 1988, pp. 35-40, vol. 23.
PCT/US2009/058603 International Search Report dated Mar. 7, 2011.
Tedford, Hugo W. et al., Functional Significance of the Beta-Hairpin in The Insecticidal Neurotoxin Omega-atracotoxin-Hvla, Journal of Biological Chemistry, American Society for Biochemistry and Molecular Biology, Inc, US, Jul. 13, 2001, pp. 26568-26576, vol. 276, No. 28.
Pfannenstiel, M. A. et al., Stability of the Larvicidal Activity of *Bacillus thuringiensis* subsp. *israelensisi*: amino acid modification and denaturants, Applied Environmental Microbiology, 1985, pp. 1196-1199, vol. 50, No. 5. Cited by 2 patents.

* cited by examiner

*Primary Examiner* — Chih-Min Kam
(74) *Attorney, Agent, or Firm* — Honigman Miller Schwartz & Cohn, LLP; Thomas A. Wootton; Jonathan P. O'Brien

(57) ABSTRACT

Procedures are described which use solvents to increase the topical insecticidal activity of toxic insect peptides. These procedures comprise drying the peptides, if needed, followed by the addition of either: 1) a polar organic solvent, with or without water, to a dried peptide, or 2) the addition of polar aprotic solvent or other adjuvant to the dried peptide, followed by the addition of either: 1) a polar organic solvent, with or without water, (where a polar aprotic solvent is added first) or 2) a polar aprotic solvent or other adjuvant to the peptide polar organic solvent (where the polar organic solvent is added first), to the peptide formulation.

3 Claims, No Drawings

```
                              SEQUENCE LISTING

<160> NUMBER OF SEQ ID NOS: 174

<210> SEQ ID NO 1
<211> LENGTH: 41
<212> TYPE: PRT
<213> ORGANISM: Atrax robustus

<400> SEQUENCE: 1

Gly Ser Gln Tyr Cys Ala Pro Ala Asp Gln Pro Cys Ser Leu Asn Thr
1               5                   10                  15

Gln Pro Cys Cys Asp Asp Val Thr Cys Thr Gln Glu Arg Asn Glu Asn
            20                  25                  30

Gly His Thr Ala Tyr Tyr Cys Arg Val
        35                  40


<210> SEQ ID NO 2
<211> LENGTH: 98
<212> TYPE: PRT
<213> ORGANISM: Hadronyche versuta

<400> SEQUENCE: 2

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30

Gly Leu Glu Ser Gln Thr Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Arg Asp Cys Cys Gly Met Thr Pro Ser Cys
65                  70                  75                  80

Thr Met Gly Leu Cys Val Pro Asn Val Gly Gly Leu Val Gly Gly Ile
                85                  90                  95

Leu Gly


<210> SEQ ID NO 3
<211> LENGTH: 98
<212> TYPE: PRT
<213> ORGANISM: Atrax robustus

<400> SEQUENCE: 3

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30
```

```
Gly Leu Glu Ser Gln Thr Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Arg Asp Cys Cys Gly Met Thr Pro Ser Cys
65                  70                  75                  80

Thr Met Gly Leu Cys Val Pro Asn Val Gly Gly Leu Val Gly Gly Ile
                85                  90                  95

Leu Gly


<210> SEQ ID NO 4
<211> LENGTH: 98
<212> TYPE: PRT
<213> ORGANISM: Hadronyche versuta

<400> SEQUENCE: 4

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu Arg Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 5
<211> LENGTH: 98
<212> TYPE: PRT
<213> ORGANISM: Hadronyche versuta

<400> SEQUENCE: 5

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser His Ala Leu His Asp Glu Ile Arg Lys Pro Ile Asn
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 6
<211> LENGTH: 98
<212> TYPE: PRT
<213> ORGANISM: Hadronyche versuta

<400> SEQUENCE: 6

Met Lys Phe Ser Lys Leu Ser Leu Thr Leu Ala Leu Ile Leu Thr Gln
1               5                   10                  15
```

```
Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 7
<211> LENGTH: 98
<212> TYPE: PRT
<213> ORGANISM: Hadronyche versuta

<400> SEQUENCE: 7

Met Lys Phe Ser Lys Leu Ser Leu Thr Leu Ala Leu Ile Leu Thr Gln
1               5                   10                  15

Val Ile Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 8
<211> LENGTH: 93
<212> TYPE: PRT
<213> ORGANISM: Hadronyche versuta

<400> SEQUENCE: 8

Met Lys Phe Ser Lys Leu Ser Leu Thr Leu Ala Leu Ile Leu Thr Gln
1               5                   10                  15

Ala Leu Phe Val Leu Cys Asp Phe Met Lys Asn Gly Leu Glu Ser Gln
            20                  25                  30

Ala Leu His Asp Glu Ile Arg Lys Ser Ile Asp Ser Glu Asn Pro Asp
        35                  40                  45

Thr Glu Arg Leu Leu Asp Cys Leu Leu Asp Asn Arg Val Cys Ser Ser
    50                  55                  60

Asp Lys Asp Cys Cys Gly Met Thr Pro Ser Cys Thr Met Gly Leu Cys
65                  70                  75                  80

Val Pro Ser Val Gly Gly Leu Val Gly Gly Ile Leu Gly
                85                  90


<210> SEQ ID NO 9
<211> LENGTH: 98
<212> TYPE: PRT
<213> ORGANISM: Atrax robustus

<400> SEQUENCE: 9
```

```
Met Lys Phe Ser Lys Leu Ser Leu Thr Leu Ala Leu Ile Leu Thr Gln
1               5                   10                  15

Val Leu Phe Val Leu Cys Gly Lys Ile Asn Glu Asp Phe Met Lys His
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 10
<211> LENGTH: 98
<212> TYPE: PRT
<213> ORGANISM: Hadronyche versuta

<400> SEQUENCE: 10

Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu His Asp Glu Ile Arg Lys Pro Ile Asn
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly


<210> SEQ ID NO 11
<211> LENGTH: 98
<212> TYPE: PRT
<213> ORGANISM: Hadronyche versuta

<400> SEQUENCE: 11

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Arg Asp Cys Cys Gly Met Thr Pro Ser Cys
65                  70                  75                  80

Thr Met Gly Leu Cys Val Pro Asn Val Gly Gly Leu Val Gly Asp Ile
                85                  90                  95

Leu Gly


<210> SEQ ID NO 12
<211> LENGTH: 97
<212> TYPE: PRT
```

<213> ORGANISM: Hadronyche versuta

<400> SEQUENCE: 12

Met Lys Phe Ser Lys Leu Ser Leu Thr Leu Ala Leu Ile Leu Thr Gln
1 5 10 15

Val Leu Phe Val Leu Cys Gly Lys Ile Glu Asp Phe Met Lys Asn Gly
20 25 30

Leu Glu Ser Gln Ala Leu His Asp Glu Ile Arg Lys Pro Ile Asp Ser
35 40 45

Glu Asn Pro Asp Thr Glu Arg Leu Leu Asp Cys Leu Leu Asp Asn Arg
50 55 60

Val Cys Ser Ser Asp Lys Asp Cys Cys Gly Met Thr Pro Ser Cys Thr
65 70 75 80

Met Gly Leu Cys Val Pro Asn Val Gly Gly Leu Val Gly Gly Ile Leu
85 90 95

Gly

<210> SEQ ID NO 13
<211> LENGTH: 93
<212> TYPE: PRT
<213> ORGANISM: Hadronyche versuta

<400> SEQUENCE: 13

Met Lys Phe Ser Lys Leu Ser Leu Thr Leu Ala Leu Ile Leu Thr Gln
1 5 10 15

Ala Leu Phe Val Leu Cys Asp Phe Met Lys Asn Gly Leu Glu Ser Gln
20 25 30

Ala Leu His Asp Glu Ile Arg Lys Pro Ile Asp Ser Glu Asn Pro Asp
35 40 45

Thr Glu Arg Leu Leu Asp Cys Leu Leu Asp Asn Arg Val Cys Ser Ser
50 55 60

Asp Lys Asp Cys Cys Gly Met Thr Pro Ser Cys Thr Met Gly Leu Cys
65 70 75 80

Val Pro Asn Val Gly Gly Leu Val Gly Gly Ile Leu Gly
85 90

<210> SEQ ID NO 14
<211> LENGTH: 98
<212> TYPE: PRT
<213> ORGANISM: Hadronyche versuta

<400> SEQUENCE: 14

Met Lys Phe Ser Lys Leu Ser Leu Thr Leu Ala Leu Ile Leu Thr Gln
1 5 10 15

Ala Leu Phe Val Leu Cys Gly Lys Ile Asn Glu Asp Phe Met Lys Asn
20 25 30

Gly Leu Glu Ser Gln Ala Leu His Asp Glu Ile Arg Lys Pro Ile Asp
35 40 45

Ser Glu Asn Pro Asp Thr Glu Arg Leu Leu Asp Cys Leu Leu Asp Asn
50 55 60

Arg Ile Cys Ser Ser Asp Lys Asp Cys Cys Gly Met Thr Pro Ser Cys
65 70 75 80

Thr Met Gly Leu Cys Val Pro Asn Val Gly Gly Leu Val Gly Gly Ile
85 90 95

Leu Gly

<210> SEQ ID NO 15

<211> LENGTH: 98
<212> TYPE: PRT
<213> ORGANISM: Hadronyche versuta

<400> SEQUENCE: 15

```
Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Lys Asn
            20                  25                  30

Gly Leu Glu Ser Gln Ala Leu His Asp Glu Ile Arg Lys Pro Ile Asp
        35                  40                  45

Ser Glu Asn Pro Asp Thr Glu Arg Leu Leu Asp Cys Leu Leu Asp Asn
    50                  55                  60

Arg Val Cys Ser Ser Asp Lys Asp Cys Cys Gly Met Thr Pro Ser Cys
65                  70                  75                  80

Thr Met Gly Leu Cys Val Pro Asn Val Gly Gly Leu Val Gly Gly Ile
                85                  90                  95

Leu Gly
```

<210> SEQ ID NO 16
<211> LENGTH: 98
<212> TYPE: PRT
<213> ORGANISM: Hadronyche versuta

<400> SEQUENCE: 16

```
Met Lys Phe Ser Lys Leu Ser Leu Thr Leu Ala Leu Ile Leu Thr Gln
1               5                   10                  15

Ala Ile Phe Val Leu Cys Gly Lys Ile Asn Glu Asp Phe Met Lys Asn
            20                  25                  30

Asp Leu Glu Ser Gln Ala Leu His Asp Glu Ile Arg Lys Pro Ile Asn
        35                  40                  45

Ser Glu Asn Pro Asp Thr Glu Arg Leu Leu Asp Cys Leu Leu Asp Ser
    50                  55                  60

Arg Val Cys Ser Ser Asp Lys Asp Cys Cys Gly Met Thr Pro Ser Cys
65                  70                  75                  80

Thr Met Gly Leu Cys Val Pro Ser Val Gly Gly Leu Val Gly Gly Ile
                85                  90                  95

Leu Gly
```

<210> SEQ ID NO 17
<211> LENGTH: 96
<212> TYPE: PRT
<213> ORGANISM: Atrax robustus

<400> SEQUENCE: 17

```
Met Lys Phe Ser Lys Leu Ser Ile Thr Leu Ala Val Ile Leu Thr Gln
1               5                   10                  15

Ala Val Phe Val Phe Cys Gly Met Thr Asn Glu Asp Phe Met Glu Lys
            20                  25                  30

Gly Leu Glu Ser Asn Glu Leu Pro Asp Ala Ile Lys Lys Pro Val Asn
        35                  40                  45

Ser Gly Lys Pro Asp Thr Lys Arg Leu Leu Asp Cys Val Leu Ser Arg
    50                  55                  60

Met Cys Phe Ser Asn Ala Asn Cys Cys Gly Leu Thr Pro Pro Cys Lys
65                  70                  75                  80

Met Gly Leu Cys Val Pro Asn Val Gly Gly Leu Leu Gly Gly Ile Leu
                85                  90                  95
```

-continued

<210> SEQ ID NO 18
<211> LENGTH: 96
<212> TYPE: PRT
<213> ORGANISM: Atrax robustus

<400> SEQUENCE: 18

```
Met Lys Phe Ser Lys Leu Ser Ile Thr Leu Ala Val Ile Leu Thr Gln
1               5                   10                  15

Ala Val Phe Val Phe Cys Gly Met Thr Asn Glu Asp Phe Met Glu Lys
            20                  25                  30

Gly Leu Glu Ser Asn Glu Leu His Asp Ala Ile Lys Lys Pro Val Asn
        35                  40                  45

Ser Gly Lys Pro Asp Thr Glu Arg Leu Leu Asp Cys Val Leu Ser Arg
    50                  55                  60

Met Cys Ser Ser Asp Ala Asn Cys Cys Gly Leu Thr Pro Thr Cys Lys
65                  70                  75                  80

Met Gly Leu Cys Val Pro Asn Val Gly Gly Leu Leu Gly Gly Ile Leu
                85                  90                  95
```

<210> SEQ ID NO 19
<211> LENGTH: 101
<212> TYPE: PRT
<213> ORGANISM: Hadronyche versuta

<400> SEQUENCE: 19

```
Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu His
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Arg Gly Leu Val Gly Gly Leu
                85                  90                  95

Leu Gly Arg Ala Leu
            100
```

<210> SEQ ID NO 20
<211> LENGTH: 101
<212> TYPE: PRT
<213> ORGANISM: Hadronyche versuta

<400> SEQUENCE: 20

```
Met Lys Phe Ser Lys Leu Ser Leu Thr Leu Ala Leu Ile Leu Thr Gln
1               5                   10                  15

Ala Leu Phe Val Leu Cys Met Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95
```

```
Leu Gly Arg Ala Leu
            100


<210> SEQ ID NO 21
<211> LENGTH: 101
<212> TYPE: PRT
<213> ORGANISM: Hadronyche versuta

<400> SEQUENCE: 21

Met Lys Phe Ser Lys Leu Ser Leu Thr Phe Ala Leu Ile Leu Thr Gln
1               5                   10                  15

Ala Leu Phe Val Leu Cys Gly Lys Ile Asn Glu Asp Phe Met Asp Asn
            20                  25                  30

Gly Leu Glu Ser His Ala Leu His Asp Glu Ile Arg Lys Pro Ile His
        35                  40                  45

Thr Glu Lys Ala Asp Ala Glu Arg Leu Val Asp Cys Val Leu Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 22
<211> LENGTH: 101
<212> TYPE: PRT
<213> ORGANISM: Hadronyche infensa

<400> SEQUENCE: 22

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu His
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 23
<211> LENGTH: 101
<212> TYPE: PRT
<213> ORGANISM: Hadronyche infensa

<400> SEQUENCE: 23

Met Lys Phe Ser Lys Leu Ser Val Thr Leu Ala Leu Ile Leu Thr Gln
1               5                   10                  15

Thr Leu Leu Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Asp Lys Ala Tyr Ala Glu Arg Val Leu Asp Cys Val Val Asn Thr
```

```
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 24
<211> LENGTH: 101
<212> TYPE: PRT
<213> ORGANISM: Hadronyche versuta

<400> SEQUENCE: 24

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 25
<211> LENGTH: 101
<212> TYPE: PRT
<213> ORGANISM: Hadronyche versuta

<400> SEQUENCE: 25

Met Lys Phe Ser Lys Leu Ser Leu Thr Leu Ala Leu Ile Leu Thr Gln
1               5                   10                  15

Ala Leu Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100


<210> SEQ ID NO 26
<211> LENGTH: 100
<212> TYPE: PRT
<213> ORGANISM: Hadronyche versuta

<400> SEQUENCE: 26

Met Lys Phe Ser Lys Leu Ser Leu Thr Leu Ala Leu Ile Leu Thr Gln
1               5                   10                  15
```

```
Ala Leu Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Leu Val Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Leu Val Gly Gly Leu Leu
                85                  90                  95

Gly Arg Ala Leu
            100


<210> SEQ ID NO 27
<211> LENGTH: 97
<212> TYPE: PRT
<213> ORGANISM: Atrax robustus

<400> SEQUENCE: 27

Met Lys Phe Ser Lys Leu Ser Ile Thr Leu Ala Val Ile Leu Thr Gln
1               5                   10                  15

Ala Val Phe Val Phe Cys Gly Met Thr Asn Glu Asp Phe Met Glu Lys
            20                  25                  30

Gly Phe Lys Ser Asn Asp Leu Gln Tyr Ala Ile Lys Gln Pro Val Asn
        35                  40                  45

Ser Gly Lys Pro Asp Thr Glu Arg Leu Leu Asp Cys Val Leu Ser Arg
    50                  55                  60

Val Cys Ser Ser Asp Glu Asn Cys Cys Gly Leu Thr Pro Thr Cys Thr
65                  70                  75                  80

Met Gly Leu Cys Val Pro Asn Val Gly Gly Leu Leu Gly Gly Leu Leu
                85                  90                  95

Ser


<210> SEQ ID NO 28
<211> LENGTH: 97
<212> TYPE: PRT
<213> ORGANISM: Atrax robustus

<400> SEQUENCE: 28

Met Lys Phe Ser Lys Leu Ser Ile Thr Leu Val Val Ile Leu Thr Gln
1               5                   10                  15

Ala Val Phe Val Phe Cys Gly Met Thr Asn Glu Asp Phe Met Glu Lys
            20                  25                  30

Gly Phe Lys Ser Asn Asp Leu Gln Tyr Ala Ile Arg Gln Pro Val Asn
        35                  40                  45

Ser Gly Lys Pro Asp Thr Glu Arg Leu Leu Asp Cys Val Leu Ser Arg
    50                  55                  60

Val Cys Ser Ser Asp Glu Asn Cys Cys Gly Leu Thr Pro Thr Cys Thr
65                  70                  75                  80

Met Gly Leu Cys Val Pro Asn Val Gly Gly Leu Leu Gly Gly Leu Leu
                85                  90                  95

Ser


<210> SEQ ID NO 29
<211> LENGTH: 101
<212> TYPE: PRT
<213> ORGANISM: Hadronyche versuta
```

<400> SEQUENCE: 29

```
Met Lys Phe Ser Lys Leu Ser Leu Thr Leu Ala Leu Ile Leu Thr Gln
1               5                   10                  15

Ala Leu Leu Val Leu Cys Gly Lys Ile Asn Glu Asp Phe Met Glu Asn
            20                  25                  30

Gly Leu Glu Ser His Ala Leu His Asp Glu Ile Arg Lys Pro Leu Asp
        35                  40                  45

Thr Glu Asn Pro Asp Thr Glu Arg Gln Leu Asp Cys Val Leu Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Asn Val Gly Gly Leu Val Gly Gly Leu
                85                  90                  95

Leu Gly Arg Ala Leu
            100
```

<210> SEQ ID NO 30
<211> LENGTH: 101
<212> TYPE: PRT
<213> ORGANISM: Hadronyche versuta

<400> SEQUENCE: 30

```
Met Lys Phe Ser Lys Leu Ser Leu Thr Leu Ala Leu Ile Leu Thr Gln
1               5                   10                  15

Val Leu Leu Val Val Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Ile Val Gly Gly Leu
                85                  90                  95

Leu Gly Arg Ala Leu
            100
```

<210> SEQ ID NO 31
<211> LENGTH: 101
<212> TYPE: PRT
<213> ORGANISM: Hadronyche versuta

<400> SEQUENCE: 31

```
Met Lys Phe Ser Lys Leu Ser Leu Thr Leu Ala Leu Ile Leu Ala Gln
1               5                   10                  15

Ala Ile Phe Val Leu Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Val Asp Cys Val Leu Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Leu Val Gly Gly Leu
                85                  90                  95

Leu Gly Arg Ala Leu
            100
```

<210> SEQ ID NO 32
<211> LENGTH: 101
<212> TYPE: PRT
<213> ORGANISM: Hadronyche versuta

<400> SEQUENCE: 32

```
Met Lys Phe Ser Lys Leu Ser Leu Thr Leu Ala Leu Ile Leu Thr Gln
1               5                   10                  15

Ala Leu Leu Val Val Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Ile
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Ile Val Gly Gly Leu
                85                  90                  95

Leu Gly Arg Ala Leu
            100
```

<210> SEQ ID NO 33
<211> LENGTH: 101
<212> TYPE: PRT
<213> ORGANISM: Hadronyche versuta

<400> SEQUENCE: 33

```
Met Lys Phe Ser Lys Leu Ser Leu Thr Leu Ala Leu Ile Leu Thr Gln
1               5                   10                  15

Ala Leu Leu Val Val Cys Gly Lys Ile Asn Glu Asp Phe Met Glu Asn
            20                  25                  30

Gly Leu Glu Ser His Ala Leu His Asp Glu Ile Arg Lys Pro Ile Asp
        35                  40                  45

Thr Glu Lys Ala Asp Ala Glu Arg Val Leu Asp Cys Val Val Asn Thr
    50                  55                  60

Leu Gly Cys Ser Ser Asp Lys Asp Cys Cys Gly Met Thr Pro Ser Cys
65                  70                  75                  80

Thr Leu Gly Ile Cys Ala Pro Ser Val Gly Gly Ile Val Gly Gly Leu
                85                  90                  95

Leu Gly Arg Ala Leu
            100
```

<210> SEQ ID NO 34
<211> LENGTH: 101
<212> TYPE: PRT
<213> ORGANISM: Hadronyche infensa

<400> SEQUENCE: 34

```
Met Lys Phe Ser Lys Leu Ser Leu Thr Leu Ala Leu Ile Leu Thr Gln
1               5                   10                  15

Ala Leu Leu Val Val Cys Gly Lys Ile Asn Glu Asp Phe Met Glu Asn
            20                  25                  30

Gly Leu Glu Ser His Ala Leu His Asp Glu Ile Arg Lys Ser Ile Asp
        35                  40                  45

Thr Glu Lys Ala Asp Ala Glu Arg Val Leu Asp Cys Val Val Asn Thr
    50                  55                  60

Leu Gly Cys Ser Ser Asp Lys Asp Cys Cys Gly Met Thr Pro Ser Cys
```

```
65                  70                  75                  80

Thr Leu Gly Ile Cys Ala Pro Ser Val Gly Gly Ile Val Gly Gly Leu
                85                  90                  95

Leu Gly Arg Ala Leu
            100


<210> SEQ ID NO 35
<211> LENGTH: 95
<212> TYPE: PRT
<213> ORGANISM: Hadronyche versuta

<400> SEQUENCE: 35

Met Lys Phe Ser Lys Leu Ser Leu Thr Phe Ala Leu Ile Leu Thr Gln
1               5                   10                  15

Thr Leu Leu Val Leu Cys Asp Phe Met Glu Asn Gly Leu Glu Ser His
            20                  25                  30

Ala Leu His Asp Glu Ile Arg Lys Pro Ile Asp Thr Glu Lys Ala Asp
        35                  40                  45

Ala Glu Arg Val Leu Asp Cys Val Val Asn Thr Leu Gly Cys Ser Ser
    50                  55                  60

Asp Lys Asp Cys Cys Gly Met Thr Pro Ser Cys Thr Leu Gly Ile Cys
65                  70                  75                  80

Ala Pro Ser Val Gly Gly Leu Val Gly Gly Leu Leu Gly Arg Ala
                85                  90                  95


<210> SEQ ID NO 36
<211> LENGTH: 76
<212> TYPE: PRT
<213> ORGANISM: Hadronyche versuta

<400> SEQUENCE: 36

Met Asn Thr Ala Thr Gly Phe Ile Val Leu Leu Val Leu Ala Thr Val
1               5                   10                  15

Leu Gly Gly Val Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Arg
    50                  55                  60

Asn Glu Asn Gly His Thr Val Tyr Tyr Cys Arg Ala
65                  70                  75


<210> SEQ ID NO 37
<211> LENGTH: 39
<212> TYPE: PRT
<213> ORGANISM: Hadronyche versuta

<400> SEQUENCE: 37

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg Ala
        35


<210> SEQ ID NO 38
<211> LENGTH: 39
<212> TYPE: PRT
<213> ORGANISM: Hadronyche versuta
```

-continued

<400> SEQUENCE: 38

Gly Ser Cys Val Pro Val Asp Gln Pro Cys Ser Leu Asn Thr Gln Pro
1 5 10 15

Cys Cys Asp Asp Ala Thr Cys Thr Gln Glu Arg Asn Glu Asn Gly His
20 25 30

Thr Val Tyr Tyr Cys Arg Ala
35

<210> SEQ ID NO 39
<211> LENGTH: 75
<212> TYPE: PRT
<213> ORGANISM: Hadronyche versuta

<400> SEQUENCE: 39

Met Asn Thr Ala Thr Gly Phe Ile Val Leu Leu Val Leu Ala Thr Ile
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Arg
50 55 60

Asn Glu Asn Gly His Thr Val Tyr Tyr Cys Arg
65 70 75

<210> SEQ ID NO 40
<211> LENGTH: 38
<212> TYPE: PRT
<213> ORGANISM: Hadronyche versuta

<400> SEQUENCE: 40

Gln Tyr Cys Val Pro Val Asp Gln Pro Cys Ser Leu Asn Thr Gln Pro
1 5 10 15

Cys Cys Asp Asp Ala Thr Cys Thr Gln Glu Arg Asn Glu Asn Gly His
20 25 30

Thr Val Tyr Tyr Cys Arg
35

<210> SEQ ID NO 41
<211> LENGTH: 75
<212> TYPE: PRT
<213> ORGANISM: Hadronyche versuta

<400> SEQUENCE: 41

Met Asn Thr Ala Thr Gly Phe Ile Val Leu Leu Val Leu Ala Thr Val
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Asp Asn Thr Val Tyr Tyr Cys Arg
65 70 75

<210> SEQ ID NO 42
<211> LENGTH: 38
<212> TYPE: PRT
<213> ORGANISM: Hadronyche versuta

<400> SEQUENCE: 42

Gln Tyr Cys Val Pro Val Asp Gln Pro Cys Ser Leu Asn Thr Gln Pro
1 5 10 15

Cys Cys Asp Asp Ala Thr Cys Thr Gln Glu Leu Asn Glu Asn Asp Asn
20 25 30

Thr Val Tyr Tyr Cys Arg
35

<210> SEQ ID NO 43
<211> LENGTH: 76
<212> TYPE: PRT
<213> ORGANISM: Hadronyche versuta

<400> SEQUENCE: 43

Met Asn Thr Ala Thr Gly Phe Ile Val Leu Leu Val Leu Ala Thr Ile
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Arg
50 55 60

Asn Glu Asn Gly His Thr Val Tyr Tyr Cys Arg Ala
65 70 75

<210> SEQ ID NO 44
<211> LENGTH: 39
<212> TYPE: PRT
<213> ORGANISM: Hadronyche versuta

<400> SEQUENCE: 44

Gln Tyr Cys Val Pro Val Asp Gln Pro Cys Ser Leu Asn Thr Gln Pro
1 5 10 15

Cys Cys Asp Asp Ala Thr Cys Thr Gln Glu Arg Asn Glu Asn Gly His
20 25 30

Thr Val Tyr Tyr Cys Arg Ala
35

<210> SEQ ID NO 45
<211> LENGTH: 76
<212> TYPE: PRT
<213> ORGANISM: Hadronyche versuta

<400> SEQUENCE: 45

Met Asn Thr Ala Thr Gly Phe Ile Val Leu Leu Val Leu Ala Thr Val
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Ala Asn Pro Val Tyr Tyr Cys Arg Ala
65 70 75

<210> SEQ ID NO 46
<211> LENGTH: 39
<212> TYPE: PRT
<213> ORGANISM: Hadronyche versuta

<400> SEQUENCE: 46

Gln Tyr Cys Val Pro Val Asp Gln Pro Cys Ser Leu Asn Thr Gln Pro
1 5 10 15

Cys Cys Asp Asp Ala Thr Cys Thr Gln Glu Leu Asn Glu Asn Ala Asn
20 25 30

Pro Val Tyr Tyr Cys Arg Ala
35

<210> SEQ ID NO 47
<211> LENGTH: 76
<212> TYPE: PRT
<213> ORGANISM: Hadronyche versuta

<400> SEQUENCE: 47

Met Asn Thr Thr Thr Gly Phe Ile Val Leu Leu Val Leu Ala Thr Ile
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Asp Asn Thr Val Tyr Tyr Cys Arg Ala
65 70 75

<210> SEQ ID NO 48
<211> LENGTH: 39
<212> TYPE: PRT
<213> ORGANISM: Hadronyche versuta

<400> SEQUENCE: 48

Gln Tyr Cys Val Pro Val Asp Gln Pro Cys Ser Leu Asn Thr Gln Pro
1 5 10 15

Cys Cys Asp Asp Ala Thr Cys Thr Gln Glu Leu Asn Glu Asn Asp Asn
20 25 30

Thr Val Tyr Tyr Cys Arg Ala
35

<210> SEQ ID NO 49
<211> LENGTH: 76
<212> TYPE: PRT
<213> ORGANISM: Hadronyche versuta

<400> SEQUENCE: 49

Met Asn Thr Ala Thr Gly Phe Ile Val Leu Leu Val Leu Ala Thr Val
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Asp Asn Thr Val Tyr Tyr Cys Arg Ala
65 70 75

<210> SEQ ID NO 50
<211> LENGTH: 39
<212> TYPE: PRT
<213> ORGANISM: Hadronyche versuta

<400> SEQUENCE: 50

Gln Tyr Cys Val Pro Val Asp Gln Pro Cys Ser Leu Asn Thr Gln Pro
1 5 10 15

Cys Cys Asp Asp Ala Thr Cys Thr Gln Glu Leu Asn Glu Asn Asp Asn
20 25 30

Thr Val Tyr Tyr Cys Arg Ala
35

<210> SEQ ID NO 51
<211> LENGTH: 76
<212> TYPE: PRT
<213> ORGANISM: Hadronyche versuta

<400> SEQUENCE: 51

Met Asn Thr Ala Thr Gly Phe Ile Val Phe Leu Val Leu Ala Thr Val
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Asp Asn Thr Val Tyr Tyr Cys Arg Ala
65 70 75

<210> SEQ ID NO 52
<211> LENGTH: 39
<212> TYPE: PRT
<213> ORGANISM: Hadronyche versuta

<400> SEQUENCE: 52

Gln Tyr Cys Val Pro Val Asp Gln Pro Cys Ser Leu Asn Thr Gln Pro
1 5 10 15

Cys Cys Asp Asp Ala Thr Cys Thr Gln Glu Leu Asn Glu Asn Asp Asn
20 25 30

Thr Val Tyr Tyr Cys Arg Ala
35

<210> SEQ ID NO 53
<211> LENGTH: 76
<212> TYPE: PRT
<213> ORGANISM: Hadronyche versuta

<400> SEQUENCE: 53

Met Asn Thr Ala Thr Gly Phe Ile Val Leu Leu Val Leu Ala Thr Val
1 5 10 15

Leu Gly Gly Ile Glu Ala Arg Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Asp Asn Thr Val Tyr Tyr Cys Arg Ala
65 70 75

<210> SEQ ID NO 54
<211> LENGTH: 39
<212> TYPE: PRT
<213> ORGANISM: Hadronyche versuta

<400> SEQUENCE: 54

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35

<210> SEQ ID NO 55
<211> LENGTH: 37
<212> TYPE: PRT
<213> ORGANISM: Hadronyche versuta

<400> SEQUENCE: 55

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35

<210> SEQ ID NO 56
<211> LENGTH: 45
<212> TYPE: PRT
<213> ORGANISM: Hadronyche versuta

<400> SEQUENCE: 56

Leu Leu Ala Cys Leu Phe Gly Asn Gly Arg Cys Ser Ser Asn Arg Asp
1               5                   10                  15

Cys Cys Glu Leu Thr Pro Val Cys Lys Arg Gly Ser Cys Val Ser Ser
            20                  25                  30

Gly Pro Gly Leu Val Gly Gly Ile Leu Gly Gly Ile Leu
        35                  40                  45

<210> SEQ ID NO 57
<211> LENGTH: 19
<212> TYPE: PRT
<213> ORGANISM: Hadronyche versuta

<400> SEQUENCE: 57

Glu Asp Thr Arg Ala Asp Leu Gln Gly Gly Glu Ala Ala Glu Lys Val
1               5                   10                  15

Phe Arg Arg

<210> SEQ ID NO 58
<211> LENGTH: 15
<212> TYPE: PRT
<213> ORGANISM: Hadronyche versuta

<400> SEQUENCE: 58

Gly Glu Ser His Val Arg Glu Asp Ala Met Gly Arg Ala Arg Arg
1               5                   10                  15

<210> SEQ ID NO 59
<211> LENGTH: 78
<212> TYPE: PRT
<213> ORGANISM: Atrax robustus

<400> SEQUENCE: 59

Met Asn Thr Ala Thr Gly Val Ile Ala Leu Leu Val Leu Ala Thr Val
1               5                   10                  15

```
Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Asn Gly Asn Thr Val Lys Arg Cys Asp
65                  70                  75


<210> SEQ ID NO 60
<211> LENGTH: 37
<212> TYPE: PRT
<213> ORGANISM: Atrax robustus

<400> SEQUENCE: 60

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35


<210> SEQ ID NO 61
<211> LENGTH: 78
<212> TYPE: PRT
<213> ORGANISM: Atrax robustus

<400> SEQUENCE: 61

Met Asn Thr Ala Thr Gly Val Ile Ala Leu Leu Val Leu Val Thr Val
1               5                   10                  15

Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Asn Gly Asn Thr Val Lys Arg Cys Asp
65                  70                  75


<210> SEQ ID NO 62
<211> LENGTH: 37
<212> TYPE: PRT
<213> ORGANISM: Atrax robustus

<400> SEQUENCE: 62

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35


<210> SEQ ID NO 63
<211> LENGTH: 78
<212> TYPE: PRT
<213> ORGANISM: Atrax robustus

<400> SEQUENCE: 63

Met Asn Thr Ala Thr Gly Val Ile Ala Leu Leu Val Leu Ala Thr Val
1               5                   10                  15
```

```
Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Thr Gly Asn Thr Val Lys Arg Cys Asp
65                  70                  75


<210> SEQ ID NO 64
<211> LENGTH: 37
<212> TYPE: PRT
<213> ORGANISM: Atrax robustus

<400> SEQUENCE: 64

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Thr Gly Asn Thr
            20                  25                  30

Val Lys Arg Cys Asp
        35


<210> SEQ ID NO 65
<211> LENGTH: 78
<212> TYPE: PRT
<213> ORGANISM: Atrax robustus

<400> SEQUENCE: 65

Met Asn Thr Ala Thr Gly Val Ile Ala Leu Leu Val Leu Ala Thr Val
1               5                   10                  15

Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Asn Ala Asn Thr Val Lys Arg Cys Asp
65                  70                  75


<210> SEQ ID NO 66
<211> LENGTH: 37
<212> TYPE: PRT
<213> ORGANISM: Atrax robustus

<400> SEQUENCE: 66

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Ala Asn Thr
            20                  25                  30

Val Lys Arg Cys Asp
        35


<210> SEQ ID NO 67
<211> LENGTH: 78
<212> TYPE: PRT
<213> ORGANISM: Atrax robustus

<400> SEQUENCE: 67

Met Asn Thr Ala Thr Gly Val Ile Ala Leu Leu Val Leu Ala Thr Val
1               5                   10                  15
```

```
Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Lys Ser Cys Thr
    50                  55                  60

Tyr Lys Glu Asn Glu Asn Gly Asn Thr Val Gln Arg Cys Asp
65                  70                  75


<210> SEQ ID NO 68
<211> LENGTH: 37
<212> TYPE: PRT
<213> ORGANISM: Atrax robustus

<400> SEQUENCE: 68

Ser Pro Thr Cys Ile Pro Ser Gly Gln Pro Cys Pro Tyr Asn Glu Asn
1               5                   10                  15

Cys Cys Ser Lys Ser Cys Thr Tyr Lys Glu Asn Glu Asn Gly Asn Thr
            20                  25                  30

Val Gln Arg Cys Asp
        35


<210> SEQ ID NO 69
<211> LENGTH: 73
<212> TYPE: PRT
<213> ORGANISM: Atrax robustus

<400> SEQUENCE: 69

Met Asn Thr Ala Thr Gly Phe Ile Val Leu Leu Val Leu Ala Thr Val
1               5                   10                  15

Leu Gly Cys Ile Glu Ala Gly Glu Ser His Val Arg Glu Asp Ala Met
            20                  25                  30

Gly Arg Ala Arg Arg Gly Ala Cys Thr Pro Thr Gly Gln Pro Cys Pro
        35                  40                  45

Tyr Asn Glu Ser Cys Cys Ser Gly Ser Cys Gln Glu Gln Leu Asn Glu
    50                  55                  60

Asn Gly His Thr Val Lys Arg Cys Val
65                  70


<210> SEQ ID NO 70
<211> LENGTH: 36
<212> TYPE: PRT
<213> ORGANISM: Atrax robustus

<400> SEQUENCE: 70

Gly Ala Cys Thr Pro Thr Gly Gln Pro Cys Pro Tyr Asn Glu Ser Cys
1               5                   10                  15

Cys Ser Gly Ser Cys Gln Glu Gln Leu Asn Glu Asn Gly His Thr Val
            20                  25                  30

Lys Arg Cys Val
        35


<210> SEQ ID NO 71
<211> LENGTH: 79
<212> TYPE: PRT
<213> ORGANISM: Hadronyche versuta

<400> SEQUENCE: 71

Met Asn Thr Ala Thr Gly Phe Ile Val Leu Leu Val Leu Ala Thr Val
1               5                   10                  15
```

```
Ile Gly Cys Ile Ser Ala Asp Phe Gln Gly Gly Phe Glu Pro Tyr Glu
            20                  25                  30

Gly Glu Asp Ala Glu Arg Ile Phe Arg Arg Ser Pro Thr Cys Ile Pro
        35                  40                  45

Thr Gly Gln Pro Cys Pro Tyr Asn Glu Asn Cys Cys Ser Gln Ser Cys
    50                  55                  60

Thr Tyr Lys Ala Asn Glu Asn Gly Asn Gln Val Lys Gly Cys Asp
65                  70                  75


<210> SEQ ID NO 72
<211> LENGTH: 37
<212> TYPE: PRT
<213> ORGANISM: Hadronyche versuta

<400> SEQUENCE: 72

Ser Pro Thr Cys Ile Pro Thr Gly Gln Pro Cys Pro Tyr Asn Glu Asn
1               5                   10                  15

Cys Cys Ser Gln Ser Cys Thr Tyr Lys Ala Asn Glu Asn Gly Asn Gln
            20                  25                  30

Val Lys Gly Cys Asp
        35


<210> SEQ ID NO 73
<211> LENGTH: 79
<212> TYPE: PRT
<213> ORGANISM: Hadronyche versuta

<400> SEQUENCE: 73

Met Asn Thr Ala Thr Gly Phe Ile Val Leu Leu Val Leu Ala Thr Val
1               5                   10                  15

Ile Gly Cys Ile Ser Ala Asp Phe Gln Gly Gly Phe Glu Pro Tyr Glu
            20                  25                  30

Glu Glu Asp Ala Glu Arg Ile Phe Arg Arg Ser Pro Thr Cys Ile Pro
        35                  40                  45

Thr Gly Gln Pro Cys Pro Tyr Asn Glu Asn Cys Cys Asn Gln Ser Cys
    50                  55                  60

Thr Tyr Lys Ala Asn Glu Asn Gly Asn Gln Val Lys Arg Cys Asp
65                  70                  75


<210> SEQ ID NO 74
<211> LENGTH: 37
<212> TYPE: PRT
<213> ORGANISM: Hadronyche versuta

<400> SEQUENCE: 74

Ser Pro Thr Cys Ile Pro Thr Gly Gln Pro Cys Pro Tyr Asn Glu Asn
1               5                   10                  15

Cys Cys Asn Gln Ser Cys Thr Tyr Lys Ala Asn Glu Asn Gly Asn Gln
            20                  25                  30

Val Lys Arg Cys Asp
        35


<210> SEQ ID NO 75
<211> LENGTH: 79
<212> TYPE: PRT
<213> ORGANISM: Hadronyche versuta

<400> SEQUENCE: 75

Met Asn Thr Ala Thr Gly Phe Ile Val Leu Leu Val Leu Ala Thr Val
1               5                   10                  15
```

-continued

```
Ile Gly Cys Ile Ser Ala Asp Phe Gln Gly Gly Phe Glu Pro Tyr Glu
            20                  25                  30

Glu Glu Asp Ala Glu Arg Ile Phe Arg Arg Ser Pro Thr Cys Ile Pro
        35                  40                  45

Thr Gly Gln Pro Cys Pro Tyr Asn Glu Asn Cys Cys Ser Gln Ser Cys
    50                  55                  60

Thr Tyr Lys Ala Asn Glu Asn Gly Asn Gln Val Lys Arg Cys Asp
65                  70                  75


<210> SEQ ID NO 76
<211> LENGTH: 37
<212> TYPE: PRT
<213> ORGANISM: Hadronyche versuta

<400> SEQUENCE: 76

Ser Pro Thr Cys Ile Pro Thr Gly Gln Pro Cys Pro Tyr Asn Glu Asn
1               5                   10                  15

Cys Cys Ser Gln Ser Cys Thr Tyr Lys Ala Asn Glu Asn Gly Asn Gln
            20                  25                  30

Val Lys Arg Cys Asp
        35


<210> SEQ ID NO 77
<211> LENGTH: 79
<212> TYPE: PRT
<213> ORGANISM: Hadronyche versuta

<400> SEQUENCE: 77

Met Asn Thr Ala Thr Gly Phe Ile Val Leu Leu Val Leu Ala Thr Val
1               5                   10                  15

Ile Gly Cys Ile Ser Val Asp Phe Gln Gly Gly Phe Glu Ser Tyr Glu
            20                  25                  30

Glu Glu Asp Ala Glu Arg Ile Phe Arg Arg Ser Pro Thr Cys Ile Pro
        35                  40                  45

Thr Gly Gln Pro Cys Pro Tyr Asn Glu Asn Cys Cys Ser Gln Ser Cys
    50                  55                  60

Thr Tyr Lys Ala Asn Glu Asn Gly Asn Gln Val Lys Arg Cys Asp
65                  70                  75


<210> SEQ ID NO 78
<211> LENGTH: 37
<212> TYPE: PRT
<213> ORGANISM: Hadronyche versuta

<400> SEQUENCE: 78

Ser Pro Thr Cys Ile Pro Thr Gly Gln Pro Cys Pro Tyr Asn Glu Asn
1               5                   10                  15

Cys Cys Ser Gln Ser Cys Thr Tyr Lys Ala Asn Glu Asn Gly Asn Gln
            20                  25                  30

Val Lys Arg Cys Asp
        35


<210> SEQ ID NO 79
<211> LENGTH: 78
<212> TYPE: PRT
<213> ORGANISM: Hadronyche versuta

<400> SEQUENCE: 79

Met Asn Thr Ala Thr Gly Phe Ile Val Leu Leu Val Leu Ala Thr Val
1               5                   10                  15
```

```
Ile Gly Cys Ile Ser Ala Asp Phe Gln Gly Gly Phe Glu Ser Ser Val
            20                  25                  30

Glu Asp Ala Glu Arg Leu Phe Arg Arg Ser Ser Thr Cys Ile Arg Thr
        35                  40                  45

Asp Gln Pro Cys Pro Tyr Asn Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 80
<211> LENGTH: 37
<212> TYPE: PRT
<213> ORGANISM: Hadronyche versuta

<400> SEQUENCE: 80

Ser Ser Thr Cys Ile Arg Thr Asp Gln Pro Cys Pro Tyr Asn Glu Ser
1               5                   10                  15

Cys Cys Ser Gly Ser Cys Thr Tyr Lys Ala Asn Glu Asn Gly Asn Gln
            20                  25                  30

Val Lys Arg Cys Asp
        35


<210> SEQ ID NO 81
<211> LENGTH: 78
<212> TYPE: PRT
<213> ORGANISM: Hadronyche versuta

<400> SEQUENCE: 81

Met Asn Thr Ala Thr Gly Phe Ile Val Leu Leu Val Leu Ala Thr Val
1               5                   10                  15

Ile Gly Cys Ile Ser Ala Asp Phe Gln Gly Gly Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr His Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 82
<211> LENGTH: 36
<212> TYPE: PRT
<213> ORGANISM: Hadronyche versuta

<400> SEQUENCE: 82

Ser Thr Cys Thr Pro Thr Asp Gln Pro Cys Pro Tyr His Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 83
<211> LENGTH: 78
<212> TYPE: PRT
<213> ORGANISM: Hadronyche versuta

<400> SEQUENCE: 83

Met Asn Thr Ala Thr Gly Phe Ile Val Leu Leu Val Leu Ala Thr Val
1               5                   10                  15
```

```
Ile Gly Cys Ile Ser Ala Asp Phe Glu Gly Ser Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr Asp Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 84
<211> LENGTH: 36
<212> TYPE: PRT
<213> ORGANISM: Hadronyche versuta

<400> SEQUENCE: 84

Ser Thr Cys Thr Pro Thr Asp Gln Pro Cys Pro Tyr Asp Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 85
<211> LENGTH: 78
<212> TYPE: PRT
<213> ORGANISM: Hadronyche versuta

<400> SEQUENCE: 85

Met Asn Thr Ala Thr Gly Phe Ile Val Leu Leu Val Leu Ala Thr Val
1               5                   10                  15

Ile Gly Cys Ile Ser Ala Asp Phe Gln Gly Ser Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr Asp Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 86
<211> LENGTH: 36
<212> TYPE: PRT
<213> ORGANISM: Hadronyche versuta

<400> SEQUENCE: 86

Ser Thr Cys Thr Pro Thr Asp Gln Pro Cys Pro Tyr Asp Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 87
<211> LENGTH: 78
<212> TYPE: PRT
<213> ORGANISM: Hadronyche versuta

<400> SEQUENCE: 87

Met Asn Thr Ala Thr Gly Phe Ile Val Leu Leu Val Leu Ala Thr Val
1               5                   10                  15
```

-continued

```
Ile Gly Cys Ile Ser Ala Asp Phe Gln Gly Ser Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr His Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 88
<211> LENGTH: 36
<212> TYPE: PRT
<213> ORGANISM: Hadronyche versuta

<400> SEQUENCE: 88

Ser Thr Cys Thr Pro Thr Asp Gln Pro Cys Pro Tyr His Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 89
<211> LENGTH: 78
<212> TYPE: PRT
<213> ORGANISM: Hadronyche versuta

<400> SEQUENCE: 89

Met Asn Thr Ala Thr Gly Phe Ile Val Leu Leu Val Leu Ala Thr Val
1               5                   10                  15

Ile Gly Cys Ile Ser Ala Asp Phe Gln Gly Gly Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr Asp Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 90
<211> LENGTH: 36
<212> TYPE: PRT
<213> ORGANISM: Hadronyche versuta

<400> SEQUENCE: 90

Ser Thr Cys Thr Pro Thr Asp Gln Pro Cys Pro Tyr Asp Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 91
<211> LENGTH: 36
<212> TYPE: PRT
<213> ORGANISM: Atrax infensus

<400> SEQUENCE: 91

Ser Thr Cys Thr Pro Thr Asp Gln Pro Cys Pro Tyr His Glu Ser Cys
1               5                   10                  15
```

```
Cys Ser Gly Ser Cys Thr Tyr Lys Ala Asn Glu Asn Gly Asn Gln Val
            20                  25                  30

Lys Arg Cys Asp
        35


<210> SEQ ID NO 92
<211> LENGTH: 37
<212> TYPE: PRT
<213> ORGANISM: Atrax infensus

<400> SEQUENCE: 92

Ser Pro Thr Cys Ile Pro Thr Gly Gln Pro Cys Pro Tyr Asn Glu Asn
1               5                   10                  15

Cys Cys Ser Gln Ser Cys Thr Tyr Lys Ala Asn Glu Asn Gly Asn Gln
            20                  25                  30

Val Lys Arg Cys Asp
        35


<210> SEQ ID NO 93
<211> LENGTH: 37
<212> TYPE: PRT
<213> ORGANISM: Atrax infensus

<400> SEQUENCE: 93

Ser Ser Thr Cys Ile Arg Thr Asp Gln Pro Cys Pro Tyr Asn Glu Ser
1               5                   10                  15

Cys Cys Ser Gly Ser Cys Thr Tyr Lys Ala Asn Glu Asn Gly Asn Gln
            20                  25                  30

Val Lys Arg Cys Asp
        35


<210> SEQ ID NO 94
<211> LENGTH: 37
<212> TYPE: PRT
<213> ORGANISM: Atrax robustus

<400> SEQUENCE: 94

Ser Ser Val Cys Ile Pro Ser Gly Gln Pro Cys Pro Tyr Asn Glu His
1               5                   10                  15

Cys Cys Ser Gly Ser Cys Thr Tyr Lys Glu Asn Glu Asn Gly Asn Thr
            20                  25                  30

Val Gln Arg Cys Asp
        35


<210> SEQ ID NO 95
<211> LENGTH: 37
<212> TYPE: PRT
<213> ORGANISM: Hadronyche versuta

<400> SEQUENCE: 95

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35


<210> SEQ ID NO 96
<211> LENGTH: 37
<212> TYPE: PRT
<213> ORGANISM: Atrax formidabillis
```

<400> SEQUENCE: 96

Ser Pro Thr Cys Thr Gly Ala Asp Arg Pro Cys Ala Ala Cys Cys Pro
1 5 10 15

Cys Cys Pro Gly Thr Ser Cys Lys Gly Pro Glu Pro Asn Gly Val Ser
20 25 30

Tyr Cys Arg Asn Asp
35

<210> SEQ ID NO 97
<211> LENGTH: 36
<212> TYPE: PRT
<213> ORGANISM: Atrax formidabillis

<400> SEQUENCE: 97

Ser Pro Thr Cys Thr Gly Ala Asp Arg Pro Cys Ala Ala Cys Cys Pro
1 5 10 15

Cys Cys Pro Gly Thr Ser Cys Lys Gly Pro Glu Pro Asn Gly Val Ser
20 25 30

Tyr Cys Arg Asn
35

<210> SEQ ID NO 98
<211> LENGTH: 37
<212> TYPE: PRT
<213> ORGANISM: Atrax formidabillis

<400> SEQUENCE: 98

Ser Pro Thr Cys Ile Arg Ser Gly Gln Pro Cys Pro Tyr Asn Glu Asn
1 5 10 15

Cys Cys Ser Gln Ser Cys Thr Phe Lys Thr Asn Glu Asn Gly Asn Thr
20 25 30

Val Lys Arg Cys Asp
35

<210> SEQ ID NO 99
<211> LENGTH: 9
<212> TYPE: PRT
<213> ORGANISM: Atrax infensus

<400> SEQUENCE: 99

Asn Gly Asn Gln Val Lys Arg Cys Asp
1 5

<210> SEQ ID NO 100
<211> LENGTH: 9
<212> TYPE: PRT
<213> ORGANISM: Atrax infensus

<400> SEQUENCE: 100

Asn Gly Asn Gln Val Lys Arg Cys Asp
1 5

<210> SEQ ID NO 101
<211> LENGTH: 9
<212> TYPE: PRT
<213> ORGANISM: Hadronyche versutus

<400> SEQUENCE: 101

Asn Gly Asn Thr Val Lys Arg Cys Asp
1 5

<210> SEQ ID NO 102

<211> LENGTH: 15
<212> TYPE: PRT
<213> ORGANISM: Hadronyche versutus

<400> SEQUENCE: 102

Ser Pro Thr Cys Ile Pro Ser Gly Gln Pro Cys Pro Tyr Asn Glu
1 5 10 15

<210> SEQ ID NO 103
<211> LENGTH: 16
<212> TYPE: PRT
<213> ORGANISM: Agelenopsis aperta

<400> SEQUENCE: 103

Glu Cys Val Pro Glu Asn Gly His Cys Arg Asp Trp Tyr Asp Glu Cys
1 5 10 15

<210> SEQ ID NO 104
<211> LENGTH: 37
<212> TYPE: PRT
<213> ORGANISM: Agelenopsis aperta

<400> SEQUENCE: 104

Glu Cys Ala Thr Lys Asn Lys Arg Cys Ala Asp Trp Ala Gly Pro Trp
1 5 10 15

Cys Cys Asp Gly Leu Tyr Cys Ser Cys Arg Ser Tyr Pro Gly Cys Met
20 25 30

Cys Arg Pro Ser Ser
35

<210> SEQ ID NO 105
<211> LENGTH: 38
<212> TYPE: PRT
<213> ORGANISM: Agelenopsis aperta

<400> SEQUENCE: 105

Ala Asp Cys Val Gly Asp Gly Gln Arg Cys Ala Asp Trp Ala Gly Pro
1 5 10 15

Tyr Cys Cys Ser Gly Tyr Tyr Cys Ser Cys Arg Ser Met Pro Tyr Cys
20 25 30

Arg Cys Arg Ser Asp Ser
35

<210> SEQ ID NO 106
<211> LENGTH: 37
<212> TYPE: PRT
<213> ORGANISM: Agelenopsis aperta

<400> SEQUENCE: 106

Ala Cys Val Gly Glu Asn Gln Gln Cys Ala Asp Trp Ala Gly Pro His
1 5 10 15

Cys Cys Asp Gly Tyr Tyr Cys Thr Cys Arg Tyr Phe Pro Lys Cys Ile
20 25 30

Cys Arg Asn Asn Asn
35

<210> SEQ ID NO 107
<211> LENGTH: 37
<212> TYPE: PRT
<213> ORGANISM: Agelenopsis aperta

<400> SEQUENCE: 107

Ala Cys Val Gly Glu Asn Lys Gln Cys Ala Asp Trp Ala Gly Pro His

-continued

```
1               5                   10                  15

Cys Cys Asp Gly Tyr Tyr Cys Thr Cys Arg Tyr Phe Pro Lys Cys Ile
            20                  25                  30

Cys Arg Asn Asn Asn
        35


<210> SEQ ID NO 108
<211> LENGTH: 37
<212> TYPE: PRT
<213> ORGANISM: Agelenopsis aperta

<400> SEQUENCE: 108

Asp Cys Val Gly Glu Ser Gln Gln Cys Ala Asp Trp Ala Gly Pro His
1               5                   10                  15

Cys Cys Asp Gly Tyr Tyr Cys Thr Cys Arg Tyr Phe Pro Lys Cys Ile
            20                  25                  30

Cys Val Asn Asn Asn
        35


<210> SEQ ID NO 109
<211> LENGTH: 36
<212> TYPE: PRT
<213> ORGANISM: Hololena curta

<400> SEQUENCE: 109

Ser Cys Val Gly Glu Tyr Gly Arg Cys Arg Ser Ala Tyr Glu Asp Cys
1               5                   10                  15

Cys Asp Gly Tyr Tyr Cys Asn Cys Ser Gln Pro Pro Tyr Cys Leu Cys
            20                  25                  30

Arg Asn Asn Asn
        35


<210> SEQ ID NO 110
<211> LENGTH: 38
<212> TYPE: PRT
<213> ORGANISM: Hololena curta

<400> SEQUENCE: 110

Ala Asp Cys Val Gly Asp Gly Gln Lys Cys Ala Asp Trp Phe Gly Pro
1               5                   10                  15

Tyr Cys Cys Ser Gly Tyr Tyr Cys Ser Cys Arg Ser Met Pro Tyr Cys
            20                  25                  30

Arg Cys Arg Ser Asp Ser
        35


<210> SEQ ID NO 111
<211> LENGTH: 70
<212> TYPE: PRT
<213> ORGANISM: Androctonus australis Hector

<400> SEQUENCE: 111

Lys Lys Asn Gly Tyr Ala Val Asp Ser Ser Gly Lys Ala Pro Glu Cys
1               5                   10                  15

Leu Leu Ser Asn Tyr Cys Asn Asn Gln Cys Thr Lys Val His Tyr Ala
            20                  25                  30

Asp Lys Gly Tyr Cys Cys Leu Leu Ser Cys Tyr Cys Phe Gly Leu Asn
        35                  40                  45

Asp Asp Lys Lys Val Leu Glu Ile Ser Asp Thr Arg Lys Ser Tyr Cys
    50                  55                  60

Asp Thr Thr Ile Ile Asn
```

65 70

<210> SEQ ID NO 112
<211> LENGTH: 70
<212> TYPE: PRT
<213> ORGANISM: Androctonus australis Hector

<400> SEQUENCE: 112

Lys Lys Asn Gly Tyr Ala Val Asp Ser Ser Gly Lys Ala Pro Glu Cys
1 5 10 15

Leu Leu Ser Asn Tyr Cys Asn Asn Glu Cys Thr Lys Val His Tyr Ala
20 25 30

Asp Lys Gly Tyr Cys Cys Leu Leu Ser Cys Tyr Cys Phe Gly Leu Asn
35 40 45

Asp Asp Lys Lys Val Leu Glu Ile Ser Asp Thr Arg Lys Ser Tyr Cys
50 55 60

Asp Thr Thr Ile Ile Asn
65 70

<210> SEQ ID NO 113
<211> LENGTH: 70
<212> TYPE: PRT
<213> ORGANISM: Androctonus australis Hector

<400> SEQUENCE: 113

Lys Lys Asp Gly Tyr Ala Val Asp Ser Ser Gly Lys Ala Pro Glu Cys
1 5 10 15

Leu Leu Ser Asn Tyr Cys Tyr Asn Glu Cys Thr Lys Val His Tyr Ala
20 25 30

Asp Lys Gly Tyr Cys Cys Leu Leu Ser Cys Tyr Cys Phe Gly Leu Asn
35 40 45

Asp Asp Lys Lys Val Leu Glu Ile Ser Asp Thr Arg Lys Ser Tyr Cys
50 55 60

Asp Thr Pro Ile Ile Asn
65 70

<210> SEQ ID NO 114
<211> LENGTH: 33
<212> TYPE: PRT
<213> ORGANISM: Scorpio maurus palmatus

<400> SEQUENCE: 114

Ala Leu Pro Leu Ser Gly Glu Tyr Glu Pro Cys Val Arg Pro Arg Lys
1 5 10 15

Cys Lys Pro Gly Leu Val Cys Asn Lys Gln Gln Ile Cys Val Asp Pro
20 25 30

Lys

<210> SEQ ID NO 115
<211> LENGTH: 61
<212> TYPE: PRT
<213> ORGANISM: Leiurus quinquestriatus

<400> SEQUENCE: 115

Asp Gly Tyr Ile Arg Lys Arg Asp Gly Cys Lys Leu Ser Cys Leu Phe
1 5 10 15

Gly Asn Glu Gly Cys Asn Lys Glu Cys Lys Ser Tyr Gly Gly Ser Tyr
20 25 30

Gly Tyr Cys Trp Thr Trp Gly Leu Ala Cys Trp Cys Glu Gly Leu Pro
35 40 45

```
Asp Glu Lys Thr Trp Lys Ser Glu Thr Asn Thr Cys Gly
    50                  55                  60


<210> SEQ ID NO 116
<211> LENGTH: 61
<212> TYPE: PRT
<213> ORGANISM: Buthotus judaicus

<400> SEQUENCE: 116

Asp Gly Tyr Ile Arg Lys Lys Asp Gly Cys Lys Val Ser Cys Ile Ile
1               5                   10                  15

Gly Asn Glu Gly Cys Arg Lys Glu Cys Val Ala His Gly Gly Ser Phe
            20                  25                  30

Gly Tyr Cys Trp Thr Trp Gly Leu Ala Cys Trp Cys Glu Asn Leu Pro
        35                  40                  45

Asp Ala Val Thr Trp Lys Ser Ser Thr Asn Thr Cys Gly
    50                  55                  60


<210> SEQ ID NO 117
<211> LENGTH: 39
<212> TYPE: PRT
<213> ORGANISM: Atrax robustus

<400> SEQUENCE: 117

Gly Ser Ser Pro Thr Cys Ile Pro Ser Gly Gln Pro Cys Pro Tyr Asn
1               5                   10                  15

Glu Asn Cys Cys Ser Gln Ser Cys Thr Phe Lys Glu Asn Glu Asn Gly
            20                  25                  30

Asn Thr Val Lys Arg Cys Asp
        35


<210> SEQ ID NO 118
<211> LENGTH: 39
<212> TYPE: PRT
<213> ORGANISM: Atrax robustus

<400> SEQUENCE: 118

Gly Ser Ala Ile Cys Thr Gly Ala Asp Arg Pro Cys Ala Ala Cys Cys
1               5                   10                  15

Pro Cys Cys Pro Gly Thr Ser Cys Lys Ala Glu Ser Asn Gly Val Ser
            20                  25                  30

Tyr Cys Arg Lys Asp Glu Pro
        35


<210> SEQ ID NO 119
<211> LENGTH: 41
<212> TYPE: PRT
<213> ORGANISM: Atrax robustus

<400> SEQUENCE: 119

Gly Ser Gln Tyr Cys Val Pro Val Asp Gln Pro Cys Ser Leu Asn Thr
1               5                   10                  15

Gln Pro Cys Cys Asp Asp Ala Thr Cys Thr Gln Glu Arg Asn Glu Asn
            20                  25                  30

Gly His Thr Val Tyr Tyr Cys Arg Ala
        35                  40


<210> SEQ ID NO 120
<211> LENGTH: 60
<212> TYPE: PRT
<213> ORGANISM: Hadronyche versuta
```

<400> SEQUENCE: 120

Met Asn Thr Ala Thr Gly Phe Ile Val Leu Leu Val Leu Ala Thr Val
1               5                   10                  15

Leu Gly Gly Val Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys
    50                  55                  60

<210> SEQ ID NO 121
<211> LENGTH: 39
<212> TYPE: PRT
<213> ORGANISM: Hadronyche versuta

<400> SEQUENCE: 121

Gln Tyr Cys Val Pro Val Asp Gln Pro Cys Ser Leu Asn Thr Gln Pro
1               5                   10                  15

Cys Cys Asp Asp Ala Tyr Cys Thr Gln Glu Arg Asn Glu Asn Gly His
            20                  25                  30

Thr Val Tyr Tyr Cys Arg Ala
        35

<210> SEQ ID NO 122
<211> LENGTH: 39
<212> TYPE: PRT
<213> ORGANISM: Hadronyche versuta

<400> SEQUENCE: 122

Gly Ser Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg Ala
        35

<210> SEQ ID NO 123
<211> LENGTH: 74
<212> TYPE: PRT
<213> ORGANISM: Hadronyche versuta

<400> SEQUENCE: 123

Met Asn Thr Ala Thr Gly Phe Ile Val Leu Leu Val Leu Ala Thr Ile
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Glu Arg Asn
    50                  55                  60

Glu Asn Gly His Thr Val Tyr Tyr Cys Arg
65                  70

<210> SEQ ID NO 124
<211> LENGTH: 38
<212> TYPE: PRT
<213> ORGANISM: Hadronyche versuta

<400> SEQUENCE: 124

```
Gln Tyr Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg
        35


<210> SEQ ID NO 125
<211> LENGTH: 75
<212> TYPE: PRT
<213> ORGANISM: Hadronyche versuta

<400> SEQUENCE: 125

Met Asn Thr Ala Thr Gly Phe Ile Val Leu Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Tyr Cys Thr Gln Glu Leu
    50                  55                  60

Asn Glu Asn Asp Asn Thr Val Tyr Tyr Cys Arg
65                  70                  75


<210> SEQ ID NO 126
<211> LENGTH: 38
<212> TYPE: PRT
<213> ORGANISM: Hadronyche versuta

<400> SEQUENCE: 126

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg
        35


<210> SEQ ID NO 127
<211> LENGTH: 76
<212> TYPE: PRT
<213> ORGANISM: Hadronyche versuta

<400> SEQUENCE: 127

Met Asn Thr Ala Thr Gly Phe Ile Val Leu Leu Val Leu Ala Thr Ile
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Arg
    50                  55                  60

Asn Glu Asn Gly His Thr Val Tyr Tyr Cys Arg Ala
65                  70                  75


<210> SEQ ID NO 128
<211> LENGTH: 39
<212> TYPE: PRT
<213> ORGANISM: Hadronyche versuta

<400> SEQUENCE: 128
```

Gln Tyr Cys Val Pro Val Asp Gln Pro Cys Ser Leu Asn Thr Gln Pro
1 5 10 15

Cys Cys Asp Asp Ala Thr Cys Thr Gln Glu Arg Asn Glu Asn Gly His
20 25 30

Thr Val Tyr Tyr Cys Arg Ala
35

<210> SEQ ID NO 129
<211> LENGTH: 76
<212> TYPE: PRT
<213> ORGANISM: Hadronyche versuta

<400> SEQUENCE: 129

Met Asn Thr Ala Thr Gly Phe Ile Val Leu Leu Val Leu Ala Thr Val
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Thr Cys Thr Gln Glu Leu
50 55 60

Asn Glu Asn Ala Asn Pro Val Tyr Tyr Cys Arg Ala
65 70 75

<210> SEQ ID NO 130
<211> LENGTH: 39
<212> TYPE: PRT
<213> ORGANISM: Hadronyche versuta

<400> SEQUENCE: 130

Gln Tyr Cys Val Pro Val Asp Gln Pro Cys Ser Leu Asn Thr Gln Pro
1 5 10 15

Cys Cys Asp Asp Ala Thr Cys Thr Gln Glu Leu Asn Glu Asn Ala Asn
20 25 30

Pro Val Tyr Tyr Cys Arg Ala
35

<210> SEQ ID NO 131
<211> LENGTH: 76
<212> TYPE: PRT
<213> ORGANISM: Hadronyche versuta

<400> SEQUENCE: 131

Met Asn Thr Thr Thr Gly Phe Ile Val Leu Leu Val Leu Ala Thr Ile
1 5 10 15

Leu Gly Gly Ile Glu Ala Gly Glu Ser His Met Arg Lys Asp Ala Met
20 25 30

Gly Arg Val Arg Arg Gln Tyr Cys Val Pro Val Asp Gln Pro Cys Ser
35 40 45

Leu Asn Thr Gln Pro Cys Cys Asp Asp Ala Tyr Cys Thr Gln Glu Leu
50 55 60

Asn Glu Asn Asp Asn Thr Val Tyr Tyr Cys Arg Ala
65 70 75

<210> SEQ ID NO 132
<211> LENGTH: 39
<212> TYPE: PRT
<213> ORGANISM: Hadronyche versuta

<400> SEQUENCE: 132

```
Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35
```

<210> SEQ ID NO 133
<211> LENGTH: 76
<212> TYPE: PRT
<213> ORGANISM: Hadronyche versuta

<400> SEQUENCE: 133

```
Met Asn Thr Ala Thr Gly Phe Ile Val Leu Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75
```

<210> SEQ ID NO 134
<211> LENGTH: 39
<212> TYPE: PRT
<213> ORGANISM: Hadronyche versuta

<400> SEQUENCE: 134

```
Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35
```

<210> SEQ ID NO 135
<211> LENGTH: 76
<212> TYPE: PRT
<213> ORGANISM: Hadronyche versuta

<400> SEQUENCE: 135

```
Met Asn Thr Ala Thr Gly Phe Ile Val Phe Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75
```

<210> SEQ ID NO 136
<211> LENGTH: 39
<212> TYPE: PRT
<213> ORGANISM: Hadronyche versuta

<400> SEQUENCE: 136

```
Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35


<210> SEQ ID NO 137
<211> LENGTH: 76
<212> TYPE: PRT
<213> ORGANISM: Atrax robustus

<400> SEQUENCE: 137

Met Asn Thr Ala Thr Gly Phe Ile Val Leu Leu Val Leu Ala Thr Val
1               5                   10                  15

Leu Gly Gly Ile Glu Ala Arg Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75


<210> SEQ ID NO 138
<211> LENGTH: 39
<212> TYPE: PRT
<213> ORGANISM: Atrax robustus

<400> SEQUENCE: 138

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35


<210> SEQ ID NO 139
<211> LENGTH: 22
<212> TYPE: PRT
<213> ORGANISM: Hadronyche versuta
<220> FEATURE:
<221> NAME/KEY: MISC_FEATURE
<222> LOCATION: (4)..(4)
<223> OTHER INFORMATION: Xaa can be any naturally occuring amino acid
<220> FEATURE:
<221> NAME/KEY: MISC_FEATURE
<222> LOCATION: (10)..(10)
<223> OTHER INFORMATION: Xaa can be any naturally occuring amino acid
<220> FEATURE:
<221> NAME/KEY: MISC_FEATURE
<222> LOCATION: (16)..(16)
<223> OTHER INFORMATION: Xaa can be any naturally occuring amino acid
<220> FEATURE:
<221> NAME/KEY: MISC_FEATURE
<222> LOCATION: (20)..(20)
<223> OTHER INFORMATION: Xaa can be any naturally occuring amino acid

<400> SEQUENCE: 139

Met Asn Thr Xaa Thr Gly Phe Ile Val Xaa Leu Val Leu Ala Thr Xaa
1               5                   10                  15

Leu Gly Gly Xaa Glu Ala
            20
```

```
<210> SEQ ID NO 140
<211> LENGTH: 15
<212> TYPE: PRT
<213> ORGANISM: Hadronyche versuta
<220> FEATURE:
<221> NAME/KEY: MISC_FEATURE
<222> LOCATION: (1)..(1)
<223> OTHER INFORMATION: Xaa can be any naturally occuring amino acid

<400> SEQUENCE: 140

Xaa Glu Ser His Met Arg Lys Asp Ala Met Gly Arg Val Arg Arg
1               5                   10                  15


<210> SEQ ID NO 141
<211> LENGTH: 64
<212> TYPE: PRT
<213> ORGANISM: Leiurus quinquestriatus hebraeus

<400> SEQUENCE: 141

Val Arg Asp Ala Tyr Ile Ala Lys Asn Tyr Asn Cys Val Tyr Glu Cys
1               5                   10                  15

Phe Arg Asp Ala Tyr Cys Asn Glu Leu Cys Thr Lys Asn Gly Ala Ser
            20                  25                  30

Ser Gly Tyr Cys Gln Trp Ala Gly Lys Tyr Gly Asn Ala Cys Trp Cys
        35                  40                  45

Tyr Ala Leu Pro Asp Asn Val Pro Ile Arg Val Pro Gly Lys Cys Arg
    50                  55                  60


<210> SEQ ID NO 142
<211> LENGTH: 64
<212> TYPE: PRT
<213> ORGANISM: Leiurus quinquestriatus quinquestriatus

<400> SEQUENCE: 142

Val Arg Asp Ala Tyr Ile Ala Lys Asn Tyr Asn Cys Val Tyr Glu Cys
1               5                   10                  15

Phe Arg Asp Ser Tyr Cys Asn Asp Leu Cys Thr Lys Asn Gly Ala Ser
            20                  25                  30

Ser Gly Tyr Cys Gln Trp Ala Gly Lys Tyr Gly Asn Ala Cys Trp Cys
        35                  40                  45

Tyr Ala Leu Pro Asp Asn Val Pro Ile Arg Val Pro Gly Lys Cys His
    50                  55                  60


<210> SEQ ID NO 143
<211> LENGTH: 65
<212> TYPE: PRT
<213> ORGANISM: Bothus occitanus tunetanus

<400> SEQUENCE: 143

Val Arg Asp Ala Tyr Ile Ala Gln Asn Tyr Asn Cys Val Tyr Phe Cys
1               5                   10                  15

Met Lys Asp Asp Tyr Cys Asn Asp Leu Cys Thr Lys Asn Gly Ala Ser
            20                  25                  30

Ser Gly Tyr Cys Gln Trp Ala Gly Lys Tyr Gly Asn Ala Cys Trp Cys
        35                  40                  45

Tyr Ala Leu Pro Asp Asn Val Pro Ile Arg Ile Pro Gly Lys Cys His
    50                  55                  60

Ser
65


<210> SEQ ID NO 144
<211> LENGTH: 64
```

<212> TYPE: PRT
<213> ORGANISM: Hottentotta judaica

<400> SEQUENCE: 144

```
Gly Arg Asp Ala Tyr Ala Leu Asp Asn Leu Asn Cys Ala Tyr Thr Cys
1               5                   10                  15

Gly Ser Lys Ser Tyr Cys Asn Thr Glu Cys Thr Lys Asn Gly Ala Val
            20                  25                  30

Ser Gly Tyr Cys Gln Trp Leu Gly Lys Tyr Gly Asn Ala Cys Trp Cys
        35                  40                  45

Ile Asn Leu Pro Asp Lys Val Pro Ile Arg Ile Pro Gly Ala Cys Arg
    50                  55                  60
```

<210> SEQ ID NO 145
<211> LENGTH: 67
<212> TYPE: PRT
<213> ORGANISM: Leiurus quinquestriatus hebraeus

<400> SEQUENCE: 145

```
Val Arg Asp Gly Tyr Ile Ala Gln Pro Glu Asn Cys Val Tyr His Cys
1               5                   10                  15

Phe Pro Gly Ser Ser Gly Cys Asp Thr Leu Cys Lys Glu Lys Gly Gly
            20                  25                  30

Thr Ser Gly His Cys Gly Phe Lys Val Gly His Gly Leu Ala Cys Trp
        35                  40                  45

Cys Asn Ala Leu Pro Asp Asn Val Gly Ile Ile Val Glu Gly Glu Lys
    50                  55                  60

Cys His Ser
65
```

<210> SEQ ID NO 146
<211> LENGTH: 66
<212> TYPE: PRT
<213> ORGANISM: Buthus occitanus mardochei

<400> SEQUENCE: 146

```
Gly Arg Asp Gly Tyr Ile Ala Gln Pro Glu Asn Cys Val Tyr His Cys
1               5                   10                  15

Phe Pro Gly Ser Ser Gly Cys Asp Thr Leu Cys Lys Glu Lys Gly Ala
            20                  25                  30

Thr Ser Gly His Cys Gly Phe Leu Pro Gly Ser Gly Val Ala Cys Trp
        35                  40                  45

Cys Asp Asn Leu Pro Asn Lys Val Pro Ile Val Val Gly Gly Glu Lys
    50                  55                  60

Cys His
65
```

<210> SEQ ID NO 147
<211> LENGTH: 65
<212> TYPE: PRT
<213> ORGANISM: Buthus occitanus mardochei

<400> SEQUENCE: 147

```
Gly Arg Asp Ala Tyr Ile Ala Gln Pro Glu Asn Cys Val Tyr Glu Cys
1               5                   10                  15

Ala Lys Asn Ser Tyr Cys Asn Asp Leu Cys Thr Lys Asn Gly Ala Lys
            20                  25                  30

Ser Gly Tyr Cys Gln Trp Leu Gly Lys Tyr Gly Asn Ala Cys Trp Cys
        35                  40                  45
```

```
Glu Asp Leu Pro Asp Asn Val Pro Ile Arg Ile Pro Gly Lys Cys His
    50                  55                  60

Phe
65


<210> SEQ ID NO 148
<211> LENGTH: 64
<212> TYPE: PRT
<213> ORGANISM: Bothus martensii Karsch

<400> SEQUENCE: 148

Val Arg Asp Ala Tyr Ile Ala Lys Pro His Asn Cys Val Tyr Glu Cys
1               5                   10                  15

Ala Arg Asn Glu Tyr Cys Asn Asp Leu Cys Thr Lys Asn Gly Ala Lys
            20                  25                  30

Ser Gly Tyr Cys Gln Trp Val Gly Lys Tyr Gly Asn Gly Cys Trp Cys
        35                  40                  45

Ile Glu Leu Pro Asp Asn Val Pro Ile Arg Val Pro Gly Lys Cys His
    50                  55                  60


<210> SEQ ID NO 149
<211> LENGTH: 64
<212> TYPE: PRT
<213> ORGANISM: Bothus martensii Karsch

<400> SEQUENCE: 149

Val Arg Asp Ala Tyr Ile Ala Lys Pro His Asn Cys Val Tyr Ser Cys
1               5                   10                  15

Ala Arg Asn Glu Trp Cys Asn Asp Leu Cys Thr Lys Asn Gly Ala Lys
            20                  25                  30

Ser Gly Tyr Cys Gln Trp Val Gly Lys Tyr Gly Asn Gly Cys Trp Cys
        35                  40                  45

Ile Glu Leu Pro Asp Asn Val Pro Ile Arg Val Pro Gly Lys Cys His
    50                  55                  60


<210> SEQ ID NO 150
<211> LENGTH: 64
<212> TYPE: PRT
<213> ORGANISM: Bothus martensii Karsch

<400> SEQUENCE: 150

Val Arg Asp Ala Tyr Ile Ala Lys Pro Glu Asn Cys Val Tyr His Cys
1               5                   10                  15

Ala Gly Asn Glu Gly Cys Asn Lys Leu Cys Thr Asp Asn Gly Ala Glu
            20                  25                  30

Ser Gly Tyr Cys Gln Trp Gly Gly Arg Tyr Gly Asn Ala Cys Trp Cys
        35                  40                  45

Ile Lys Leu Pro Asp Asp Val Pro Ile Arg Val Pro Gly Lys Cys His
    50                  55                  60


<210> SEQ ID NO 151
<211> LENGTH: 66
<212> TYPE: PRT
<213> ORGANISM: Bothus martensii Karsch

<400> SEQUENCE: 151

Val Arg Asp Gly Tyr Ile Ala Leu Pro His Asn Cys Ala Tyr Gly Cys
1               5                   10                  15

Leu Asn Asn Glu Tyr Cys Asn Asn Leu Cys Thr Lys Asp Gly Ala Lys
            20                  25                  30
```

```
Ile Gly Tyr Cys Asn Ile Val Gly Lys Tyr Gly Asn Ala Cys Trp Cys
        35                  40                  45

Ile Gln Leu Pro Asp Asn Val Pro Ile Arg Val Pro Gly Arg Cys His
    50                  55                  60

Pro Ala
65


<210> SEQ ID NO 152
<211> LENGTH: 64
<212> TYPE: PRT
<213> ORGANISM: Leiurus quinquestriatus

<400> SEQUENCE: 152

Val Arg Asp Gly Tyr Ile Ala Gln Pro Glu Asn Cys Val Tyr His Cys
1               5                   10                  15

Ile Pro Asp Cys Asp Thr Leu Cys Lys Asp Asn Gly Gly Thr Gly Gly
            20                  25                  30

His Cys Gly Phe Lys Leu Gly His Gly Ile Ala Cys Trp Cys Asn Ala
        35                  40                  45

Leu Pro Asp Asn Val Gly Ile Ile Val Asp Gly Val Lys Cys His Lys
    50                  55                  60


<210> SEQ ID NO 153
<211> LENGTH: 66
<212> TYPE: PRT
<213> ORGANISM: Leiurus quinquestriatus

<400> SEQUENCE: 153

Val Arg Asp Gly Tyr Ile Ala Lys Pro Glu Asn Cys Ala His His Cys
1               5                   10                  15

Phe Pro Gly Ser Ser Gly Cys Asp Thr Leu Cys Lys Glu Asn Gly Gly
            20                  25                  30

Thr Gly Gly His Cys Gly Phe Lys Val Gly His Gly Thr Ala Cys Trp
        35                  40                  45

Cys Asn Ala Leu Pro Asp Lys Val Gly Ile Ile Val Asp Gly Val Lys
    50                  55                  60

Cys His
65


<210> SEQ ID NO 154
<211> LENGTH: 66
<212> TYPE: PRT
<213> ORGANISM: Centruroides noxius

<400> SEQUENCE: 154

Lys Glu Gly Tyr Leu Val Asp Ile Lys Asn Thr Gly Cys Lys Tyr Glu
1               5                   10                  15

Cys Leu Lys Leu Gly Asp Asn Asp Tyr Cys Leu Arg Glu Cys Lys Gln
            20                  25                  30

Gln Tyr Gly Lys Gly Ala Gly Gly Tyr Cys Tyr Ala Phe Ala Cys Trp
        35                  40                  45

Cys Thr His Leu Tyr Glu Gln Ala Ile Val Trp Pro Leu Pro Asn Lys
    50                  55                  60

Arg Cys
65


<210> SEQ ID NO 155
<211> LENGTH: 66
<212> TYPE: PRT
<213> ORGANISM: Centruroides noxius
```

-continued

```
<400> SEQUENCE: 155

Lys Glu Gly Tyr Leu Val Glu Leu Gly Thr Gly Cys Lys Tyr Glu Cys
1               5                   10                  15

Phe Lys Leu Gly Asp Asn Asp Tyr Cys Leu Arg Glu Cys Lys Ala Arg
            20                  25                  30

Tyr Gly Lys Gly Ala Gly Gly Tyr Cys Tyr Ala Phe Gly Cys Trp Cys
        35                  40                  45

Thr Gln Leu Tyr Glu Gln Ala Val Val Trp Pro Leu Lys Asn Lys Thr
    50                  55                  60

Cys Arg
65


<210> SEQ ID NO 156
<211> LENGTH: 66
<212> TYPE: PRT
<213> ORGANISM: Centruroides suffusus suffusus

<400> SEQUENCE: 156

Lys Glu Gly Tyr Leu Val Ser Lys Ser Thr Gly Cys Lys Tyr Glu Cys
1               5                   10                  15

Leu Lys Leu Gly Asp Asn Asp Tyr Cys Leu Arg Glu Cys Lys Gln Gln
            20                  25                  30

Tyr Gly Lys Ser Ser Gly Gly Tyr Cys Tyr Ala Phe Ala Cys Trp Cys
        35                  40                  45

Thr His Leu Tyr Glu Gln Ala Val Val Trp Pro Leu Pro Asn Lys Thr
    50                  55                  60

Cys Asn
65


<210> SEQ ID NO 157
<211> LENGTH: 66
<212> TYPE: PRT
<213> ORGANISM: Centruroides suffusus suffusus

<400> SEQUENCE: 157

Lys Glu Gly Tyr Leu Val Asn Ser Tyr Thr Gly Cys Lys Phe Glu Cys
1               5                   10                  15

Phe Lys Leu Gly Asp Asn Asp Tyr Cys Leu Arg Glu Cys Arg Gln Gln
            20                  25                  30

Tyr Gly Lys Gly Ser Gly Gly Tyr Cys Tyr Ala Phe Gly Cys Trp Cys
        35                  40                  45

Thr His Leu Tyr Glu Gln Ala Val Val Trp Pro Leu Pro Asn Lys Thr
    50                  55                  60

Cys Asn
65


<210> SEQ ID NO 158
<211> LENGTH: 76
<212> TYPE: PRT
<213> ORGANISM: Buthotus judaicus

<400> SEQUENCE: 158

Lys Lys Asn Gly Tyr Pro Leu Asp Arg Asn Gly Lys Thr Thr Glu Cys
1               5                   10                  15

Ser Gly Val Asn Ala Ile Ala Pro His Tyr Cys Asn Ser Glu Cys Thr
            20                  25                  30

Lys Val Tyr Val Ala Glu Ser Gly Tyr Cys Cys Trp Gly Ala Cys Tyr
        35                  40                  45
```

```
Cys Phe Gly Leu Glu Asp Asp Lys Pro Ile Gly Pro Met Lys Asp Ile
    50                  55                  60

Thr Lys Lys Tyr Cys Asp Val Gln Ile Ile Pro Ser
65                  70                  75


<210> SEQ ID NO 159
<211> LENGTH: 70
<212> TYPE: PRT
<213> ORGANISM: Androctonus australis Hector

<400> SEQUENCE: 159

Lys Lys Asn Gly Tyr Ala Val Asp Ser Ser Gly Lys Ala Pro Glu Cys
1               5                   10                  15

Leu Leu Ser Asn Tyr Cys Asn Asn Glu Cys Thr Lys Val His Tyr Ala
            20                  25                  30

Asp Lys Gly Tyr Cys Cys Leu Leu Ser Cys Tyr Cys Phe Gly Leu Asn
        35                  40                  45

Asp Asp Lys Lys Val Leu Glu Ile Ser Asp Thr Arg Lys Ser Tyr Cys
    50                  55                  60

Asp Thr Thr Ile Ile Asn
65                  70


<210> SEQ ID NO 160
<211> LENGTH: 70
<212> TYPE: PRT
<213> ORGANISM: Leiurus quinquestriatus quinquestriatus

<400> SEQUENCE: 160

Lys Lys Asn Gly Tyr Ala Val Asp Ser Ser Gly Lys Ala Pro Glu Cys
1               5                   10                  15

Leu Leu Ser Asn Tyr Cys Tyr Asn Glu Cys Thr Lys Val His Tyr Ala
            20                  25                  30

Asp Lys Gly Tyr Cys Cys Leu Leu Ser Cys Tyr Cys Val Gly Leu Ser
        35                  40                  45

Asp Asp Lys Lys Val Leu Glu Ile Ser Asp Ala Arg Lys Lys Tyr Cys
    50                  55                  60

Asp Phe Val Thr Ile Asn
65                  70


<210> SEQ ID NO 161
<211> LENGTH: 70
<212> TYPE: PRT
<213> ORGANISM: Leiurus quinquestriatus hebraeus

<400> SEQUENCE: 161

Lys Lys Asn Gly Phe Ala Val Asp Ser Asn Gly Lys Ala Pro Glu Cys
1               5                   10                  15

Phe Phe Asp His Tyr Cys Asn Ser Glu Cys Thr Lys Val Tyr Tyr Ala
            20                  25                  30

Glu Lys Gly Tyr Cys Cys Leu Leu Ser Cys Tyr Cys Phe Gly Leu Asn
        35                  40                  45

Asp Asp Lys Lys Val Leu Glu Ile Ser Asp Thr Thr Lys Lys Tyr Cys
    50                  55                  60

Asp Phe Thr Ile Ile Asn
65                  70


<210> SEQ ID NO 162
<211> LENGTH: 72
<212> TYPE: PRT
<213> ORGANISM: Bothus martensii Karsch
```

<400> SEQUENCE: 162

Lys Lys Asn Gly Tyr Ala Val Asp Ser Ser Gly Lys Val Ala Glu Cys
1 5 10 15

Leu Phe Asn Asn Tyr Cys Asn Asn Glu Cys Thr Lys Val Tyr Tyr Ala
20 25 30

Asp Lys Gly Tyr Cys Cys Leu Leu Lys Cys Tyr Cys Phe Gly Leu Leu
35 40 45

Asp Asp Lys Pro Val Leu Asp Ile Trp Asp Ser Thr Lys Asn Tyr Cys
50 55 60

Asp Val Gln Ile Ile Asp Leu Ser
65 70

<210> SEQ ID NO 163
<211> LENGTH: 61
<212> TYPE: PRT
<213> ORGANISM: Leiurus quinquestriatus hebraeus

<400> SEQUENCE: 163

Asp Gly Tyr Ile Lys Arg Arg Asp Gly Cys Lys Val Ala Cys Leu Ile
1 5 10 15

Gly Asn Glu Gly Cys Asp Lys Glu Cys Lys Ala Tyr Gly Gly Ser Tyr
20 25 30

Gly Tyr Cys Trp Thr Trp Gly Leu Ala Cys Trp Cys Glu Gly Leu Pro
35 40 45

Asp Asp Lys Thr Trp Lys Ser Glu Thr Asn Thr Cys Gly
50 55 60

<210> SEQ ID NO 164
<211> LENGTH: 60
<212> TYPE: PRT
<213> ORGANISM: Leiurus quinquestriatus hebraeus

<400> SEQUENCE: 164

Asp Gly Tyr Ile Arg Gly Asp Gly Cys Lys Val Ser Cys Val Ile Asn
1 5 10 15

His Val Phe Cys Asp Asn Glu Cys Lys Ala Ala Gly Gly Ser Tyr Gly
20 25 30

Tyr Cys Trp Ala Trp Gly Leu Ala Cys Trp Cys Glu Gly Leu Pro Ala
35 40 45

Glu Arg Glu Trp Lys Tyr Glu Thr Asn Thr Cys Gly
50 55 60

<210> SEQ ID NO 165
<211> LENGTH: 62
<212> TYPE: PRT
<213> ORGANISM: Buthotus judaicus

<400> SEQUENCE: 165

Asp Gly Tyr Ile Arg Lys Lys Asp Gly Cys Lys Val Ser Cys Ile Ile
1 5 10 15

Gly Asn Glu Gly Cys Arg Lys Glu Cys Val Ala His Gly Gly Ser Phe
20 25 30

Gly Tyr Cys Trp Thr Trp Gly Leu Ala Cys Trp Cys Glu Asn Leu Pro
35 40 45

Asp Ala Val Thr Trp Lys Ser Ser Thr Asn Thr Cys Gly Arg
50 55 60

<210> SEQ ID NO 166
<211> LENGTH: 61

<212> TYPE: PRT
<213> ORGANISM: Buthacus arenicola

<400> SEQUENCE: 166

Asp Gly Tyr Ile Arg Arg Arg Asp Gly Cys Lys Val Ser Cys Leu Phe
1 5 10 15

Gly Asn Glu Gly Cys Asp Lys Glu Cys Lys Ala Tyr Gly Gly Ser Tyr
20 25 30

Gly Tyr Cys Trp Thr Trp Gly Leu Ala Cys Trp Cys Glu Gly Leu Pro
35 40 45

Asp Asp Lys Thr Trp Lys Ser Glu Thr Asn Thr Cys Gly
50 55 60

<210> SEQ ID NO 167
<211> LENGTH: 61
<212> TYPE: PRT
<213> ORGANISM: Leiurus quinquestriatus quinquestriatus

<400> SEQUENCE: 167

Asp Gly Tyr Ile Arg Lys Arg Asp Gly Cys Lys Leu Ser Cys Leu Phe
1 5 10 15

Gly Asn Glu Gly Cys Asn Lys Glu Cys Lys Ser Tyr Gly Gly Ser Tyr
20 25 30

Gly Tyr Cys Trp Thr Trp Gly Leu Ala Cys Trp Cys Glu Gly Leu Pro
35 40 45

Asp Asp Lys Thr Trp Lys Ser Glu Thr Asn Thr Cys Gly
50 55 60

<210> SEQ ID NO 168
<211> LENGTH: 60
<212> TYPE: PRT
<213> ORGANISM: Bothus occitanus tunetanus

<400> SEQUENCE: 168

Asp Gly Tyr Ile Lys Gly Tyr Lys Gly Cys Lys Ile Thr Cys Val Ile
1 5 10 15

Asn Asp Asp Tyr Cys Asp Thr Glu Cys Lys Ala Glu Gly Gly Thr Tyr
20 25 30

Gly Tyr Cys Trp Lys Trp Gly Leu Ala Cys Trp Cys Glu Asp Leu Pro
35 40 45

Asp Glu Lys Arg Trp Lys Ser Glu Thr Asn Thr Cys
50 55 60

<210> SEQ ID NO 169
<211> LENGTH: 63
<212> TYPE: PRT
<213> ORGANISM: Leiurus quinquestriatus hebraeus

<400> SEQUENCE: 169

Asp Asn Gly Tyr Leu Leu Asn Lys Ala Thr Gly Cys Lys Val Trp Cys
1 5 10 15

Val Ile Asn Asn Ala Ser Cys Asn Ser Glu Cys Lys Leu Arg Arg Gly
20 25 30

Asn Tyr Gly Tyr Cys Tyr Phe Trp Lys Leu Ala Cys Tyr Cys Glu Gly
35 40 45

Ala Pro Lys Ser Glu Leu Trp Ala Tyr Ala Thr Asn Lys Cys Asn
50 55 60

<210> SEQ ID NO 170
<211> LENGTH: 62

<212> TYPE: PRT
<213> ORGANISM: Tityus serrulatus

<400> SEQUENCE: 170

```
Lys Glu Gly Tyr Leu Met Asp His Glu Gly Cys Lys Leu Ser Cys Phe
1               5                   10                  15

Ile Arg Pro Ser Gly Tyr Cys Gly Arg Glu Cys Gly Ile Lys Lys Gly
            20                  25                  30

Ser Ser Gly Tyr Cys Tyr Ala Trp Pro Ala Cys Tyr Cys Tyr Gly Leu
        35                  40                  45

Pro Asn Trp Val Lys Val Trp Asp Arg Ala Thr Asn Lys Cys
    50                  55                  60
```

<210> SEQ ID NO 171
<211> LENGTH: 64
<212> TYPE: PRT
<213> ORGANISM: Tityus zulianus

<400> SEQUENCE: 171

```
Lys Asp Gly Tyr Leu Val Gly Asn Asp Gly Cys Lys Tyr Ser Cys Phe
1               5                   10                  15

Thr Arg Pro Gly Thr Tyr Cys Ala Asn Glu Cys Ser Arg Val Lys Gly
            20                  25                  30

Lys Asp Gly Tyr Cys Tyr Ala Trp Met Ala Cys Tyr Cys Tyr Ser Met
        35                  40                  45

Pro Asn Trp Val Lys Thr Trp Asp Arg Ala Thr Asn Arg Cys Gly Arg
    50                  55                  60
```

<210> SEQ ID NO 172
<211> LENGTH: 29
<212> TYPE: PRT
<213> ORGANISM: Oldenlandia affinis

<400> SEQUENCE: 172

```
Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25
```

<210> SEQ ID NO 173
<211> LENGTH: 29
<212> TYPE: PRT
<213> ORGANISM: Oldenlandia affinis

<400> SEQUENCE: 173

```
Cys Gly Glu Thr Cys Phe Gly Gly Thr Cys Asn Thr Pro Gly Cys Ser
1               5                   10                  15

Cys Thr Trp Pro Ile Cys Thr Arg Asp Gly Leu Pro Val
            20                  25
```

<210> SEQ ID NO 174
<211> LENGTH: 30
<212> TYPE: PRT
<213> ORGANISM: Oldenlandia affinis

<400> SEQUENCE: 174

```
Gly Thr Pro Cys Gly Glu Ser Cys Val Tyr Ile Pro Cys Ile Ser Gly
1               5                   10                  15

Val Ile Gly Cys Ser Cys Thr Asp Lys Val Cys Tyr Leu Asn
            20                  25                  30
```

PEPTIDE TOXIN FORMULATION

This application is a continuation application of U.S. application Ser. No. 13/528,402, filed Jun. 20, 2012, now U.S. Pat. No. 8,501,684, which is a divisional of U.S. application Ser. No. 12/568,400, filed Sep. 28, 2009, issued as U.S. Pat. No. 8,271,003, which claims the priority of U.S. Provisional Application No. 61/101,825, filed Oct. 1, 2008, all of which are incorporated herein by reference in their entirety.

SEQUENCE LISTING

This application incorporates by reference in its entirety the Sequence Listing entitled "Family_G_US_AMENDED-_SEQ_LISTING__2014__01__13_ST25.txt" (104,095 bytes) which was created on Jan. 13, 2014 and filed electronically herewith on Jan. 14, 2014. This Sequence Listing was also submitted on two compact disks labeled "COPY 1 REPLACEMENT Jan. 13, 2014" and "COPY 2 REPLACEMENT Jan. 13, 2014", which was created on Jan. 13, 2014 and mailed Jan. 14, 2014.

FIELD OF THE INVENTION

This invention relates to the field of formulations for insecticidal peptides.

BACKGROUND

Insecticidal peptides are toxic to their targets when delivered internally, but sometimes they have little or no topical activity. Topical insecticidal activity refers to a toxin's ability to inhibit the growth, impair the movement or even kill an insect when the toxin is delivered to the insect or the insect's environment by spraying, or other means, as opposed to delivering the toxin directly to the insect's gut or internal organs by injection or inducing the insect to consume the toxin from its food, for example an insect feeding upon a transgenic plant.

The ability to successfully enhance or even change the properties of peptides with solvents has, until now, proven elusive. The wide variety, unique properties and special nature of peptides, combined with the huge variety of possible solvents one could choose from, has produced only a few described methods for the enhancement of a few selected peptides in the past 50 years or so. Various texts on the subject exist. See for example, *Principles of Dairy Chemistry Jenness and Patton* (1959) pp. 115-117, 127, 317, 326-328, 333.

Attempts have been made to enhance the activity of a few peptides through purification and extraction. For example, U.S. Pat. No. 5,840,838, Hensley, describes a procedure for enhancing the activity of amyloid β peptide, a 39-43 residue peptide, with a process that involves dissolving the peptide in an organic solvent, incubating it for 45 minutes to 3 hours above room temperature, equilibrating to room temperature and then removing the solvent.

U.S. Pat. No. 4,530,784, Rosenberg, relates to a method of extracting a biologically active factor that restores contact inhibition of growth to malignant cells in mammals by mixing specially prepared media with a volatile non-denaturing precipitating agent. The precipitate formed by this reaction is separated from the formulation and extracted with a biologically acceptable ionic buffering agent.

U.S. Pat. No. 4,337,194, Diaz, is a process of preparing somatostatin using a step-wise peptide coupling reaction in a solution of DMF. The product of the reaction is isolated by evaporation or by precipitation with a second solvent which renders the somatostatin insoluble, then the crude peptide obtained is purified.

There are few if any descriptions, however, for a method to convert a peptide which has low topical insecticidal activity into one having significantly greater topical insecticidal activity.

The procedure described here increases the topical insecticidal toxicity of insecticidal peptides. Peptides thus treated are referred to herein as "enhanced topical peptides." The process described herein of making enhanced topical peptides is sometimes called making the peptides "special." The process of making the peptides special makese the peptides more active than before they are treated with the process or treatment described herein. Once the peptides have been made special they can be applied topically to the insect, the insect's environment, to the places it inhabits, its habitat and to the food it touches, eats or consumes; in order to control the insect, rather than having to engineer the peptide into the genome of a suitable plant or other food. Both the new process, the formulations, and the new enhanced topical peptides produced by the process are described and claimed herein.

SUMMARY OF THE INVENTION

Procedures are described which use solvents to increase the toxicity of toxic insect peptides. Those procedures involve the preparation of the peptides by drying the peptides, if needed, followed by the addition of either: 1) a polar organic solvent, with or without water, to a dried peptide, or 2) a polar aprotic solvent or other adjuvant to the dried peptide, followed by the addition of either: 1) a polar organic solvent, with or without water, (where a polar aprotic solvent is added first or 2) a polar aprotic solvent or other adjuvant to the peptide polar organic solvent (where the polar organic solvent is added first), to the peptide formulation.

The procedures can also be described as follows: A method of increasing the topical insecticidal activity of a toxic insect peptide, herein called making the peptide special comprising: adding either i) a polar organic solvent or ii) a polar aprotic solvent or adjuvant to the peptide and then adding either i) a polar organic solvent or ii) a polar aprotic solvent or adjuvant, which ever was not added initially to the initial peptide formulation of above.

A method is described herein where the polar organic solvent comprises from about 50, to about 99.9 percent (%) of the final volume of the formulation. The method is specifically described where the polar organic solvent comprises from about 60, 70, 85, 90 to about 99.0 percent (%) of the final volume of the formulation. The method is described wherein the polar organic solvent comprises from about 70, to about 99.0 percent (%) of the final volume of the formulation. The method is specifically described wherein the polar organic solvent comprises from about 60, 70, 80, 85, 90, to about 99.0 percent (%) of the final volume of the formulation. The polar organic solvent may be selected from acetone, methanol, ethanol, propanol and all its isomers, methyl ethyl ketone, diethyl ketone, acetonitrile, ethyl acetoacetate. The polar organic solvents selected from acetone, methanol, ethanol, propanol and all its isomers are especially useful.

The polar aprotic solvent or adjuvant will comprise from about 20%, to about 0.001%, of the final volume of the formulation. Specifically the polar aprotic solvent or adjuvant, comprises from about 15%, to about 0.005%, from about 10%, to about 0.01%, from about 8%, to about 0.1%, from about 5%, to about 0.1%, of the final volume of the formulation. The polar aprotic solvent or adjuvant is selected from dimethyl sulfoxide, dimethylformamide, dioxane and hexamethylphosphorotriamide. Dimethyl sulfoxide, also known as DMSO is exemplified.

The toxic insect peptides are preferably those with a) greater than 10 amino acid residues and less than 3000 amino acid residues; b) a molecular weight from about 550 Da to about 350,000 Da; and c) they have insecticidal activity. The peptides may optionally have 1 to 5 disulfide bonds. The insecticidal activity of the peptides optionally are peptides having topical activity in at least one reproducable topical insecticidal assay. The toxic insect peptides may be selected from the venom of a spider, mite, scorpion, snake, snails, certain plants or any combination thereof. The spider may be an Australian funnel web spider, and peptides from the genus of *Atrax* or *Hadronyche* are easily made special using the procedures described herein. Specific peptides from spiders, scorpions and plants are provided in the sequence listing.

Disclosed are formulations of special toxic peptides comprising: a) a peptide; b) a polar organic solvent; c) a polar aprotic solvent or adjuvant; d) wherein said polar organic solvent comprises from about 80, to about 99 percent (%) of the final volume of the formulation; e) wherein said polar aprotic solvent or adjuvant comprises from about 1, to about 10 percent (%) of the final volume of the suspension; and t) an optional water phase, wherein said water phase comprises from 0 (zero), to about 10 percent (%) of the final volume of the suspension.

The peptides made special by the process of this invention are new and may be separately claimed. These peptides are described by all of their properties and not simply their sequence. For the most part the peptide sequence information of the peptides which can be made special, as described herein, are known; however, once treated the same peptides will have greated topical activity. These peptides made special are novel with unique properties, both the peptides and the process of making them are disclosed and claimed herein.

Methods to control insects are also disclosed, in particular applications of the special toxic peptides or special toxic peptide formulations applied to the insect's environment. The special toxic peptide may be applied as a dry or liquid formulation. The formulation may include wetting and dispersing agents, surfactants and other common components of insecticidal peptide formulations. Also, described are special toxic peptides produced as the product of any of the processes described herein. The processes described herein can be used with any peptides. The following peptides are mentioned by way of specific examples and are not intended to limit the range, type or number of peptides can be made special using this process.

DETAILED DESCRIPTION OF THE INVENTION

Definitions

"Active ingredient" means a peptide or polypeptide, herein it is sometimes called a toxin.

"Insecticidal activity", "insect control" or "control the insect" means that on or after exposure of the insect to the active ingredient, the insect either dies, stops or slows its movement or its feeding, stops or slows its growth, fails to pupate, cannot reproduce or cannot produce fertile offspring.

"Insect('s) environment" means any place or surface that is or will be exposed to an insect. The insect's environment includes the places it inhabits, its habitat and the food it touches, eats or consumes.

"Toxic insect peptide" means a peptide having insecticidal activity when ingested by or injected into an insect but having little, low or no topical insecticidal activity.

"Peptide made special" means the same as "Special topical peptide" below.

"Polar aprotic solvents" are organic solvents that have ion dissolving power but lack an acidic hydrogen. A polar aprotic solvent cannot donate hydrogen ($H^+$ or proton.) These solvents generally have high dielectric constants and high polarity. Further examples that should be considered representative and not limiting are; dimethyl sulfoxide (DMSO), dimethylformamide, dioxane, hexamethylphosphorotriamide and methyl sulfoxide (MSO®). Adjuvants as polar aprotic solvents. Certain adjuvants can also be polar aprotic solvents. Mixtures of oils with surfactants, commonly referred to as adjuvants are other examples of polar aprotic solvents. Crop oils in combination with surfactants can also act as polar aprotic solvents. Examples such as Agicide Activator®, Herbimax®, Maximizer®, and MSO® all available from Loveland company serve to demonstrate the commercial adjuvants can act as the polar aprotic solvents as the term is defined by this invention. MSO® is a methylated seed oil and surfactant blend that uses methyl esters of soya oil in amounts of between about 80 and 85 percent petroleum oil with 15 to 20 percent surfactant. Use and descriptions of MSO® used as a polar aprotic solvent can be found in Example 7.

"Polar organic solvents" are organic solvents with dipole moments sufficient to confer a dielectric constant of 15 or higher, acetone being one example. Other examples of polar organic solvents include compounds with a dissociable $H^+$, such as lower alkyl alcohols. Further examples that should be considered representative and not limiting are as follows: acetone, methanol, ethanol, propanol, all isomers of propanol including 1- and 2-, propanol (n- and iso-propanol, respectively). Other polar organic solvents which might be successfully used as part of this formulation can be determined by those skilled in the art; these may include methyl ethyl ketone, diethyl ketone, acetonitrile, ethyl acetoacetate, etc.

"Special topical peptide" means a peptide previously having low topical insecticidal activity that has relatively higher topical insecticidal activity because of the procedures described herein used to increase the topical activity of peptides.

"Topical activity" or "topical insecticidal activity" means insecticidal activity that results from exposure or contact of the insect's outer layers, to the insecticidal peptide. Topical activity can result from exposure to or contact between a treated material or surface and the external part of the insect, such as its feet, abdomen, antenna, mouth. Topical activity can result from insect preening of external parts of the insect followed by ingestion of the toxin. Treatment of any material or surface with insecticide or toxin that then comes in contact with the insect with resultant insecticidal activity is considered a topical activity.

"Topical application" means the application of the active ingredient to an insect's environment, or the insect itself. An insect's environment may be treated with a "topical application" in any manner including: spraying, painting, baiting, impregnating materials, such as treating paper or other objects that are then placed in the same area when the insect is known or expected to visit or frequent. Topical application can also mean direct contact with the insect and the insecticide.

The Process to Make Special

Description of the Process to Make Peptides Special.

Add a polar organic solvent, with or without water, to a dried peptide and then add a polar aprotic solvent or other adjuvant to the peptide polar organic solvent (optional water) formulation, or in the alternative first add a polar aprotic solvent or other adjuvant to a dried peptide and then add a polar organic solvent (with or without water) to the polar aprotic solvent peptide formulation. Additional treatments and pretreatments to the peptides and peptide solvent formulations are optional and are discussed below.

The peptides made special are then used as desired for effect. Application and use of the peptides made special may be with any means, either standard or as determined to be effective by a practicioner who is skilled in the art, including but not limited to: spraying through an atomizer or other type of spray nozzle, direct/indirect application of droplets of the formulation, application of the dried residue of the formulation to any body surface of the targeted insect, immersion of the targeted insect in a bath, etc.

The peptide is made special upon completion of the addition of the polar organic solvent and the polar aprotic solvent or other adjuvant, with the solvents added in either order. It is better to start with a peptide that is in a non-aqueous environment. The preferred order of solvent addition will be determined by a practicioner who is skilled in the art of insecticidal formulation, giving attention and consideration to the particular peptides used. Numerous variations of the manner in which the solvent is added can be made and should be apparent to one skilled in the art. Some variations and more details of the procedure are provided below.

Preparation of the peptide by removing water may be needed if the starting peptides are dissolved in water. The procedure of making the peptides special may be practiced with peptides having either high or low solubility in water. Often peptides are prepared in water based solvents or expressed in aqueous environments. If the peptide to be made special is in an aqueous environment, most of the water should first be removed, i.e. the peptide should be dried. If the peptide is already in a dried state, then drying is not needed. Preparation of peptides can involve concentrating, purifying, isolating or identifying peptides and or the amounts or concentration of the peptide in the sample. Once the peptide is in a preferred state, condition or concentration, it should be "dried." One method of drying a peptide, or taking it out of an aqueous environment, is to lyophilize the peptide using traditional peptide lyophilization procedures. See Protein Analysis and Purification $2^{nd}$ Ed. Rosenberg 2005 pp 140. Other methods include, but are not limited to, spray drying, rotary evaporation, and vacuum centrifugation. Peptide drying should be done in a manner such that the peptides are not unduly damaged or destroyed. Excessive heat should be avoided. Those skilled in the art will know and be able to practice appropriate procedures to dry the peptide.

Adding the polar organic solvent to the dried peptide. Once the peptide is prepared by having most of the water removed, it is ready for mixing with either the polar organic solvent or the polar aprotic solvent or adjuvant. Better results are sometimes obtained when the polar organic solvent is added to the dried peptide before the polar aprotic solvent is added and order is described below, but with some peptides in some situations the polar aprotic solvent is added to the dried peptide followed by addition of the polar organic solvent.

The Polar Organic Solvent.

Many polar organic solvents can be used, some seem to produce peptides having greater topical activity than others. We have found the following polar organic solvents work well in this procedure to make peptides special: acetone, methanol, ethanol, propanol, all isomers of propanol including 1- and 2-, propanol (n- and iso-propanol, respectively). Other polar organic solvents which might be successfully used as part of this formulation can be determined by those skilled in the art; these may include methyl ethyl ketone, diethyl ketone, acetonitrile, ethyl acetoacetate, etc. The mixing of peptide and solvent can be done with any laboratory method of mixing such as vortex mixing, stirring, shaking, etc.

If the polar organic solvent is added to the dried peptide before the aprotic solvent/adjuvant then it (the polar organic solvent) can be as much as about 98 to 100% of the liquid in the formulation, and the peptide will likely form a precipitate in the solvent. The formulation may appear as a cloudy or hazy suspension. It should be vigorously mixed. The polar organic solvent can have some water in it, see "Water" below, but pure or dry solvent also works well. Optimal final concentrations of water and polar organic solvent can be determined for a formulation of a particular special topical peptide by those skilled in the art. We have formulated special topical peptides with polar organic solvent at final concentrations of 80 to 99%. Lower concentrations than 80% would also work with some peptides. We specifically describe polar organic solvents at final concentrations of 60, 70, 80, 81, 82, 83, 84, 85, 86, 87, 88, 89, 90, 91, 92, 93, 94, 95, 96, 97, 98 and 99% and with water at final concentrations of 0% to 10%, in particular final water concentrations of 1, 2, 3, 4, 5, 6, 7, 8, 9 and 10% are described. Those skilled in the art will be able to successfully use values outside these sample ranges for particular formulations of particular special topical peptides.

Sonication.

Once the peptide is properly taken up in the solvent it may be sonicated or otherwise treated to further increase its topical activity. Sonication may break up the peptide particles in solution and reduce the size of the suspended particles. Sonication or other procedures to reduce particle size appears to increase topical toxicity of the peptides. Other procedures that reduce particle size, in addition to sonication, may be used to increase topical activity. Various procedures to reduce particle size should be known to those familiar with peptide manipulation. Without being limited to any particular procedure or mechanism, using a high speed blender, shaking or stirring with glass beads may also be useful to increase the toxicity of the special toxic peptides.

Water.

As mentioned above, the polar organic solvent does not need to be pure or absolute when used: it can contain water. Moreover, this water may contain salts, organic molecules, peptides, etc. Water can presumably be added to the peptide either before the polar organic solvent is added to the peptide formulation, or at the same time or after addition of the polar organic solvent. Care should be taken not to use too large a concentration of water, as we have observed that this can reduce or eliminate the activity of certain formulations of certain special topical peptides. The water need not be pure, it can include various proteins such as chitinases, phospholipases, lectins, etc., or salts, sugars, carbohydrates, etc., in order to create a more useful and stable final solution. Alternatively, the water phase can initially be pure water and then various proteins such as chitinases, phospholipases, lectins etc. could be added to the water phase after it is mixed with the polar organic solvent and the peptides.

The Polar Aprotic Solvent.

The polar aprotic solvent or adjuvant can be used as the first ingredient added to the dried peptide or it can be added to the peptide polar organic solvent (water optional) formulation described above. Those skilled in the art can determine whether the polar aprotic solvent or the polar organic solvent should be the first liquid added to the dried peptide in order to determine the better way to make the peptides special. This determination will depend on the circumstances of each case and in particular exactly which toxic insect peptide is used and the final formulation desired. However, such variations should be practiced with care, as we have observed that in some cases lower insecticidal activity resulted if the polar aprotic solvent was added to the peptide before the polar organic solvent is added.

Polar aprotic solvents lack an acidic hydrogen. These solvents generally have high dielectric constants and high polarity. Examples include dimethyl sulfoxide, dimethylformamide, dioxane and hexamethylphosphorotriamide.

The adjuvant can be any oil and/or emulsifying surfactant formulated for agricultural application of pesticides and especially peptides. These commercial formulations typically have oils and emulsifying surfactants formulated to "carry and spread" the active ingredients. Examples include: "Aero Dyneamic" from Helena Chemical Co. which has methylated or ethylated vegetable oil, a nonionic surfactant and a buffering agent or acidifier. It is further described as a "proprietary blend of ethoxylated alkyl phosphate esters, polyalkylene modified polydimethylsiloxane, nonionic emulsifiers and methylated vegetable oils. For aerial use only at 2-8 qt/100 gal. 30-70 percent. Provides pH reduction and buffering, NIS and oil blend" See label for rates. Further examples and manufactures of adjuvants can be found in Table 1.

TABLE 1

Agrochemical Surfactants.

| Surfactant/Adjuvant | Composition | Brief Description | Suggested Application |
|---|---|---|---|
| LI 700 (Loveland Products) | Phosphatidylcholine, methylacetic acid, and alkyl polyoxyethylene ether (80%); Constituents ineffective as spray adjuvant (20%) | Non-ionic low foaming penetrant; aids in providing uniform spray coverage and to acidify spray solutions | 8-24 oz/100 gallon (0.0625%-0.1825% solution) |
| SILWET L-77 (Loveland Products) | Polysiloxane polyether copolymer, polyether (100%) | Non-ionic, organofunctional silicone surfactant which lower's surface tension below commonly used surfactants, resulting in more effective wetting and more uniform coverage | 3-16 oz/100 gal (0.02%-0.125% solution) |
| MSO Concentrate w/LECI-TECH (Loveland Products) | Methylated vegetable oil, alcohol ethoxylate, phosphatidylcholine (100%) | Enhances activity of post applied herbicides non-ionic surfactants and petroleum-based crop oils | 1-2 pints per acre (1.25-2.5% based on 10 gal/acre) |
| TACTIC (Loveland Products) | Synthetic latex, 1,2-propanediol, Alcohol ethoxylate, silicone polyether copolymer (63.4%); Constituents ineffective as spray adjuvant (36.6%) | Increases adherence (latex polymer) and coverage (organosilicone) | 8-32 oz/100 gal. (0.0625%-0.25% solution) |

Optimal final concentrations of polar aprotic solvent and/or adjuvant can be determined for the formulation of a particular topical peptide made special by those skilled in the art. We have successfully formulated special topical peptides with polar aprotic solvent at final concentrations of 10% and as low as 0.01%, with 0.5% working well. The adjuvant Silwet L-77, for example, works well at a final concentration as low as 0.01%, and those skilled in the art should be able to successfully find other adjuvants using even higher or lower values than the ranges described here for particular formulations of particular topical peptides made special.

The water and sonication steps described above can be applied in any order. Particular modes of insecticidal application for particular formulations of special topical peptides will be determined by those skilled in the art.

Topical Toxic Peptides and their Preparation.

Examples of toxic insect peptides are well known and can be found in numerous references. They can be identified by their peptidic nature and their activity, usually oral or injection insecticidal activity. Here we provide a few examples to better illustrate and describe the invention, but the invention is not limited to these examples. All of these examples and others not shown here are descriptive of new materials, described and claimed here for the first time.

Toxic insect peptides are peptides of greater than 5 amino acid residues and less than 3000 amino acid residues. They range in molecular weight from about 550 Da to about 350,000 Da. Toxic insect peptides have some type of insecticidal activity. Typically they show activity when injected into insects but most do not have significant activity when applied to an insect topically. The insecticidal activity of toxic insect peptides is measured in a variety of ways. Common methods of measurement are widely known to those skilled in the art. Such methods include, but are not limited to determination of median response doses (e.g., $LD_{50}$, $PD_{50}$, $LC_{50}$, $ED_{50}$) by fitting of dose-response plots based on scoring various parameters such as: paralysis, mortality, failure to gain weight, etc. Measurements can be made for cohorts of insects exposed to various doses of the insecticidal formulation in question. Analysis of the data can be made by creating curves defined by probit analysis and/or the Hill Equation, etc. In such cases, doses would be administered by hypodermic injection, by hyperbaric infusion, by presentation of the insecticidal formulation as part of a sample of food or bait, etc.

Toxic insect peptides are defined here as all peptides shown to be insecticidal upon delivery to insects either by hypodermic injection, hyperbaric infusion, or upon per os delivery to an insect (i.e., by ingestion as part of a sample of food presented to the insect). This class of peptides thus comprises, but is not limited to, many peptides produced naturally as components of the venoms of spiders, mites, scorpions, snakes, snails, etc. This class also comprises, but is not limited to, various peptides produced by plants (e.g., various lectins, ribosome inactivating proteins, and cysteine proteases), and various peptides produced by entomopathogenic microbes (e.g. the Cry1/delta endotoxin family of proteins produced by various *Bacillus* species.)

The following documents are incorporated by reference in the US in their entirely, in other jurisdictions where allowed and they are of common knowledge given their publication. In addition they are incorporated by reference and known specifically for their sequence listings to the extent they describe peptide sequences. See the following:

U.S. Pat. No. 5,763,568, issued Jun. 9, 1998, specifically the sequences in the sequence listing, and those numbered 1-26, and those known as "kappa" or "omega" toxins, including those that can form 2-4 intrachain disulphide bridges, and the peptides appearing on columns 2 and 4, and Table 5, and in FIG. 5, FIG. 15, FIG. 16, FIG. 17, FIG. 18. U.S. Pat. No. 5,959,182, issued Sep. 28, 1999, specifically the sequences in the sequence listing, and those numbered 1-26 and those known as "kappa" or "omega" toxins, including toxins that can form 2-4 intrachain disulphide bridges, and the peptides appearing on columns 2 and 4, and Table 5, and in FIG. 5, FIG. 15, FIG. 16, FIG. 17, FIG. 18. U.S. Pat. No. 6,583,264 B2, issued Jun. 24, 2003, and U.S. Pat. No. 7,173,106 B2, issued Feb. 6, 2007 specifically sequence number 1, named "omega-atracotoxin-Hv2a or w-atracotoxin-Hv2a, including toxins that can form 2-4 intrachain disulphide bridges. U.S. Pat. No. 7,279,547 B2, issued Oct. 9, 2007, specifically the sequences in the sequence listing, and those numbered 1-35, and variants of ω-atracotoxin-Hv2a, toxins that can form 2-4 intrachain disulphide bridges, and the peptides appearing on columns 4-8 of the specification, and in FIG. 3 and FIG. 4. U.S. Pat. No. 7,354,993 B2, issued Apr. 8, 2008 specifically the peptide sequences listed in the sequence listing, and those numbered 1-39, and those named U-ACTX polypeptides, toxins that can form 2-4 intrachain disulphide bridges, and variants thereof, and the peptides appearing on columns 4-9 of the specification and in FIG. 1. EP patent 1 812 464 B1, published and granted Aug. 10, 2008 Bulletin 2008/41, specifically the peptide sequences listed in the sequence listing, toxins that can form 2-4 intrachain disulphide bridges, and those as numbered 1-39, and those named U-ACTX polypeptides, and variants thereof, and the peptides appearing in paragraphs 0023 to 0055, and appearing in FIG. 1.

Described and incorporated by reference to the peptides identified herein are homologous variants of sequences mentioned, have homology to such sequences or referred to herein which are also identified and claimed as suitable for making special according to the processes described herein including but not limited to all homologous sequences including homologous sequences having at least any of the following percent identities to any of the sequences disclosed her or to any sequence incorporated by reference: 30%, 35%, 40%, 45%, 50%, 55%, 60%, 65%, 70%, 75%, 80%, 85%, 90% or 95% or greater identity to any and all sequences identified in the patents noted above, and to any other sequence identified herein, including each and every sequence in the sequence listing of this application. When the term homologous or homology is used herein with a number such as 30% or greater then what is meant is percent identity or percent similarity between the two peptides. When homologous or homology is used without a numeric percent then it refers to two peptide sequences that are closely related in the evolutionary or developmental aspect in that they share common physical and functional aspects like topical toxicity and similar size within 100% greater length or 50% shorter length or peptide.

Described and incorporated by reference to the peptides identified herein that are derived from any source mentioned in the US and EP patent documents referred to above, including but not limited to the following: Toxins isolated from plants and insects, especially toxins from spiders, scorpions and plants that prey on or defend themselves from insects, such as, funnel web spiders and especially Australian funnel web spiders, including toxins found in, isolated from or derived from the genus *Atrax* or *Hadronyche*, including the genus species, *Hadronyche versuta*, or the Blue Mountain funnel web spider, *Atrax robustus, Atrax formidabilis, Atrax infensus* including toxins known as "atracotoxins," "co-atracotoxins," "kappa" atracotoxins, "omega" atracotoxins also known as co-atracotoxin, U-ACTX polypetides, U-ACTX-Hv1a, rU-ACTX-Hv1a, rU-ACTX-Hv1b, or mutants or variants, especially peptides of any of these types and especially those less than about 200 amino acids but greater than about 10 amino acids, and especially peptides less than about 150 amino acids but greater than about 20 amino acids, especially peptides less than about 100 amino acids but greater than about 25 amino acids, especially peptides less than about 65 amino acids but greater than about 25 amino acids, especially peptides less than about 55 amino acids but greater than about 25 amino acids, especially peptides of about 37 or 39 or about 36 to 42 amino acids, especially peptides with less than about 55 amino acids but greater than about 25 amino acids, especially peptides with less than about 45 amino acids but greater than about 35 amino acids, especially peptides with less than about 115 amino acids but greater than about 75 amino acids, especially peptides with less than about 105 amino acids but greater than about 85 amino acids, especially peptides with less than about 100 amino acids but greater than about 90 amino acids, including peptide toxins of any of the lengths mentioned here that can form 2, 3 and or 4 or more intrachain disulphide bridges, including toxins that disrupt calcium channel currents, including toxins that disrupt potassium channel currents, especially insect calcium channels or hybrids thereof, especially toxins or variants thereof of any of these types, and any combination of any of the types of toxins described herein that have topical insecticidal activity, can be made special by the processes described herein.

Venomous peptides from the Australian Funnel Web Spider, genus *Atrax* and *Hadronyche* are particularly suitable and work well when treated by the methods, procedures or processes described by this invention. These spider peptides, like many other toxic peptides, including especially are toxic scorpion and toxic plant peptides, become topically active or toxic when treated by the processes described by this invention. Examples of suitable peptides tested and with data are provided herein. In addition to the organisms mentioned above, the following species are also specifically know to carry toxins suitable for being made special by the process of this invention. The following species are specifically named: *Agelenopsis aperta, Androctonus australis Hector, Antrax formidabillis, Antrax infensus, Atrax robustus, Bacillus thuringiensis, Bothus martensii Karsch, Bothus occitanus tunetanus, Buthacus arenicola, Buthotus judaicus, Buthus occitanus mardochei, Centruroides noxius, Centruroides suffusus suffusus, Hadronyche infensa, Hadronyche versuta, Hadronyche versutus, Hololena curta, Hottentotta judaica, Leiurus quinquestriatus, Leiurus quinquestriatus hebraeus, Leiurus quinquestriatus quinquestriatus, Oldenlandia affinis, Scorpio maurus palmatus, Tityus serrulatus, Tityus zulianu*. Any peptidic toxins from any of the genus listed above and or genus species are suitable for being made special according to the process in this invention.

The Examples in this specification are not intended to, and should not be used to limit the invention, they are provided only to illustrate the invention.

As noted above, many peptides are suitable candidates as the subject of the process to make special. The sequences noted above, below and in the sequence listing are especially suitable peptides that can be made special, and many of these have been made special according to this invention with the results shown in the examples below.

```
(one letter code)
                                                    SEQ ID NO: 60
SPTCI PSGQP CPYNE NCCSQ SCTFK ENENG NTVKR CD
1   5    10    15    20    25    30    35 37

(three letter code)
                                                    SEQ ID NO: 60
Ser Pro Thr Cys Ile Pro Ser Gly Gln Pro Cys Pro Tyr Asn Glu Asn
 1               5                  10                  15

Cys Cys Ser Gln Ser Cys Thr Phe Lys Glu Asn Glu Asn Gly Asn Thr
            20                  25                  30

Val Lys Arg Cys Asp
        35      37
```

Named "ω-ACTX-Hv1a" it has disulfide bridges at positions: 4-18, 11-22 and 17-36. The molecular weight is 4096.

```
(one letter code)
                                                   SEQ ID NO: 117
GSSPT CIPSG QPCPY NENCC SQSCT FKENE NGNTV KRCD
1   5    10    15    20    25    30    35   39

(three letter code)
                                                   SEQ ID NO: 117
Gly Ser Ser Pro Thr Cys Ile Pro Ser Gly Gln Pro Cys Pro Tyr Asn
 1               5                  10                  15

Glu Asn Cys Cys Ser Gln Ser Cys Thr Phe Lys Glu Asn Glu Asn Gly
            20                  25                  30

Asn Thr Val Lys Arg Cys Asp
        35              39
```

Named "ω-ACTX-Hv1a+2" it has disulfide bridges at positions: 6-20, 13-24 and 19-38. The molecular weight is 4199.

```
(one letter code)
                                                   SEQ ID NO: 118
GSAIC TGADR PCAAC CPCCP GTSCK AESNG VSYCR KDEP
1   5    10    15    20    25    30    35   39

(three letter code)
                                                   SEQ ID NO: 118
Gly Ser Ala Ile Cys Thr Gly Ala Asp Arg Pro Cys Ala Ala Cys Cys
 1               5                  10                  15

Pro Cys Cys Pro Gly Thr Ser Cys Lys Ala Glu Ser Asn Gly Val Ser
            20                  25                  30

Tyr Cys Arg Lys Asp Glu Pro
        35              39
```

Named "rκ-ACTX-Hv1c" it has disulfide bridges at positions: 5-19, 12-24, 15-16, 18-34. The molecular weight is 3912.15

```
(one letter code)
                                                   SEQ ID NO: 119
GSQYC VPVDQ PCSLN TQPCC DDATC TQERN ENGHT VYYCR A

1   5    10    15    20    25    30    35    40 41
```

-continued

```
(three letter code)
                                            SEQ ID NO: 119
Gly Ser Gln Tyr Cys Val Pro Val Asp Gln Pro Cys Ser Leu Asn Thr
 1               5                  10                  15

Gln Pro Cys Cys Asp Asp Ala Thr Cys Thr Gln Glu Arg Asn Glu Asn
            20                  25                  30

Gly His Thr Val Tyr Tyr Cys Arg Ala
        35                  40  41
```

Named "rU-ACTX-Hv1a ("Hybrid")+2" it has disulfide bridges at positions: 5-20, 12-25, 19-39. The molecular weight is 4570.51

Preparation of the Topical Toxic Peptides

The toxic peptides described above can be prepared in a variety of ways and in some embodiments they need not be prepared by any formal process. The peptides can simply be collected with or without other impurities in a composition and utilized. In one embodiment in which several Examples are provided below, the peptides are lyophylized or they have some, most or nearly all liquid removed prior to being made special. In some embodiments the peptides are still wet and only excess liquid is removed. In some embodiments the peptides are in aqueous solutions or in something similar to an aqueous solution. The peptides need not be isolated or purified prior to being made special.

Reproducible Assays to Measure Topical Insecticidal Activity.

The topical insecticidal activity of a peptide can be measured and quantified. Numerous assays are available. Several examples of reproducible assays useful to determine the topical activity of a peptide are provided in the examples below. These examples describe both peptide and assay in detail but they should not be used to limit the scope of the claims or invention.

Materials and Methods

EXAMPLES

Example 1

Topical Assay with Acetone and DMSO Using House Fly

Toxin is ω-ACTX-Hv1a:

```
                                      (SEQ ID NO: 60)
SPTCIPSGQPCPYNENCCSQSCTFKENENGNTVKRCD
```

Synthetic. Molecular weight: 4050 Da. $LD_{50}$ in House-fly: 90.2 pmol/g

Administration and application of the formulation.

Insect is House fly (*Musca domestica*) from Benzon research weighing between 12-20 mg (average mass 16 mg) would each receive 2 μL micropipette applications of formulations onto the dorsal thoracic surface of the body.

Toxin Doses:

90,000 pmol/g ω-ACTX (1000×Injection LD50) dissolved in 90% Acetone/10% DMSO or DMSO (10%-20%) with 0.1% Tween 20, 9,000 pmol/g (100×Injection LD50), and 900 pmol/g (10×LD50) dissolved in DMSO (10-20%) with 0.1% Tween 20.

Preparation of Water-Based Application Solutions

ω-ACTX/DMSO stock—3.5 mg lyophilized ω-ACTX (Auspep) massed and dissolved in 70 μL DMSO (50 μg/μL stock). Water+Tween stocks−1000 μL aliquots of Tween 20 stocks were prepared in water to the percent volume to volume values (listed below) from a 1% Tween 20 stock (e.g. 111 μL 1% Tween 20+889 μL water for the 0.111% Tween 20 stock, etc.). In all cases, the Tween 20 stock was added to the tube first, then DMSO, and finally the ω-ACTX/DMSO stock.

TABLE 2

Water-DMSO Treatments.

| ω-ACTX Dose (pmol/g) | [DMSO] (%) | ω-ACTX | DMSO | Water + Tween (% v/v) | Final Volume |
|---|---|---|---|---|---|
| 90,000 | 10% | 17.5 μL ω-ACTX STOCK (50 μg/μL in DMSO) | 12.5 μL | 270 μL (0.111% Tween) | 300 μL |
| −ve | 10% | — | 30 μL | 270 μL (0.111% Tween) | 300 μL |
| 90,000 | 20% | 17.5 μL ω-ACTX STOCK (50 μg/μL in DMSO) | 42.5 μL | 240 μL (0.125% Tween) | 300 μL |
| 9,000 | 20% | 30 μL 90,000 pmol/g ACTX Solution | 54 μL | 216 μL (0.138% Tween) | 300 μL |
| 900 | 20% | 30μL 9,000 pmol/g ACTX Solution | 54 μL | 216 μL (0.138% Tween) | 300 μL |

TABLE 2-continued

| Water-DMSO Treatments. | | | | | |
|---|---|---|---|---|---|
| ω-ACTX Dose (pmol/g) | [DMSO] (%) | ω-ACTX | DMSO | Water + Tween (% v/v) | Final Volume |
| −ve | 20% | — | 60 μL | 240 μL (0.125% Tween) | 300 μL |

Note.
In Table 2 and many Tables below some or all of the following abbreviations are used: "twitch" or "twch" means twitching; "morb" means moribund and "−ve" means "negative control conditions" which is the same as experimental conditions but without any active ingredient (s).

Preparation of Acetone-Based Application Solutions:

Acetone—The same 50 μg/μL ω-ACTX stock in DMSO was used to create a formulation in 90% acetone and 10% DMSO that would deliver a dose equivalent of 90,000 pmol/g when applied as a 2 μL droplet to houseflies of an average mass of 16 mg. In this case, the toxin stock was added to the acetone first, and then a final volume of DMSO was added to reach 10% m/v DMSO. This was done to examine the amount of precipitate when dissolved toxin was added to acetone.

A second ω-ACTX solution was also prepared by dissolving 1.2 mg lyophilized ω-ACTX (Auspep) in 240 μL acetone (5 μg/μL stock). 50 μL of this stock was diluted in 121.5 μL of Acetone after which 17.15 μL DMSO was added (10% concentration). Calculations leading to an estimate the ω-ACTX dosage for this formulation are as follows:

50 μL×5 μg/μL ω-ACTX stock=250 μg ω-ACTX÷171.5 μL total volume=1.458 μg/μL×2 μL/insect=2.915 μg/insect 2.915 μg/insect×1 μmol/4050 μg×$10^6$ pmol/1 μmol=719.7 μmol/insect×1 insect/0.016 g=45,000 μmol/g A control formulation of bovine serum albumin (BSA) was also prepared in acetone and DMSO. Due to the concentration of the stock BSA, the concentration of acetone was only about 60% in 10% DMSO.

TABLE 3

| Acetone-DMSO Treatments | | | | | |
|---|---|---|---|---|---|
| ω-ACTX Dose (pmol/g) | DMSO Concentration (%) | ω-ACTX | DMSO | Acetone | Final Volume |
| 90,000 | 10% | 17.5 μL ω-ACTX STOCK (50 μg/μL in DMSO) | 12.5 μL | 270 μL | 300 μL |
| 45,000 | 10% | 50 μL (5 μg/μL in Acetone) | 17.15 μL | 104.3 μL | 171.5 μL |
| −ve | 10% | — | 30 μL | 270 μL | 300 μL |
| +ve | 10% | 87.5 μL 10 μg/mL BSA | 30 μL | 182.5 μL | 300 μL |

Administration and Application of the Formulation

Houseflies were refrigerated for ~4 hr and then anesthetized with $CO_2$. Each treatment formulation described above was applied to a group of ten anesthetized flies. The treatments consisted of a 2 μL droplet of the respective formulation, pipetted onto the dorsal thoracic body surface of a fly. Groups of ten anesthetized flies were used to test each treatment regime. The Acetone/DMSO solution rapidly evaporated from the cuticle. The DMSO formulations were allowed to absorb through the cuticle. Treated flies which revived on their dorsal surface tended to stick to the bottom of the bin and struggle following placement with food and water; intervention was made to prevent this by gently tapping the bin or manipulating stuck flies back to an upright orientation with tweezers. A control group of untreated flies was also reserved to ensure mortality was not affected by $CO_2$ exposure. All treatments were given food and water and observed for 24 hours.

Results (n=10 for all treatment groups, number of dead flies per group reported in second column):

TABLE 4

| Results of Acetone-DMSO Treatments | | |
|---|---|---|
| Treatment (Time Applied) | Dead (Time post treatment) | Notes |
| −ve 20% DMSO/Tween (3:54PM Jul. 1, 2008) | 0 (~8 hr) | All flies healthy/active |
| 90,000 pmol/g ω-ACTX 20% DMSO/Tween (4:09PM Jul. 1, 2008) | 1 (~8 hr) | 1 dead in food, others healthy |
| 9,000 pmol/g ω-ACTX 20% DMSO/Tween (4:22PM Jul. 1, 2008) | 1 (~7.5 hr) | 1 stuck to bottom(?) dead(?) |
| 900 pmol/g ω-ACTX 20% DMSO/Tween (4:32PM Jul. 1, 2008) | 0 (~7.5 hr) | |
| −ve 10% DMSO/Tween (5:39PM Jul. 1, 2008) | 0 (~6.5 hr) | 1 stuck to bottom & dislodged |
| 90,000 pmol/g ω-ACTX 10% DMSO/Tween (4:52PM Jul. 1, 2008) | 0 (~7 hr) | |
| −ve 90% Acetone/10% DMSO (5:25PM Jul. 1, 2008) | 1 <~7.5 hr) | |
| +ve BSA Protein (5:01PM Jul. 1, 2008) | 1(?) (~7 hr) | 1 unresponsive on side of food dish |
| 90,0000 pmol/g ω-ACTX (DMSO Stock) 90%Acetone/10% DMSO (5:11PM Jul. 1, 2008) | 0 (~7 hr) | 1 stuck on back & dislodged |
| 45,0000 pmol/g ω-ACTX (Acetone Stock) 90%Acetone/10% DMSO (5:19PM Jul. 1, 2008) | 1 (~6.5 hr) | 1 dead in food dish |
| −ve untreated (5:40PM Jul. 1, 2008) | 0 (~6.5 hr) | |
| −ve 20% DMSO/Tween (3:54PM Jul. 1, 2008) | 0 (~19 hr) | All flies healthy/active |
| 90,000 pmol/g ω-ACTX 20% DMSO/Tween (4:09PM Jul. 1, 2008) | 1 (~19 hr) | 1 twitching |
| 9,000 pmol/g ω-ACTX 20% DMSO/Tween (4:22PM Jul. 1, 2008) | 1 (~18.5 hr) | Dead from sticking to bottom |
| 900 pmol/g ω-ACTX 20% DMSO/Tween (4:32PM Jul. 1, 2008) | 0 (~18.5 hr) | All flies healthy/active |
| −ve 10% DMSO/Tween (5:39PM Jul. 1, 2008) | 1 (~17.5 hr) | Dead in food |
| 90,000 pmol/g ω-ACTX 10% DMSO/Tween (4:52PM Jul. 1, 2008) | 1 (18 hr) | 2 twitching |
| −ve 90% Acetone/10%DMSO (5:25PM Jul. 1, 2008) | 1 (~17.5 hr) | |
| +ve BSA Protein (5:01PM Jul. 1, 2008) | 1 (~18 hr) | |
| 90,0000 pmol/g ω-ACTX (DMSO Stock) 90% Acetone/10% DMSO (5:11PM Jul. 1, 2008) | 1 (~18 hr) | 1 twitching |
| 45,0000 pmol/g ω-ACTX (Acetone Stock) 90%Acetone/10% DMSO (5:19PM Jul. 1, 2008) | 5 (~17.5 hr) | 2 twitching |
| −ve untreated (5:40PM Jul. 1, 2008) | 0 (~17.5 hr) | All flies healthy/active |
| Treatment | Dead (Time post treatment) | Notes |
| −ve 20% DMSO/Tween (3:54PM Jul. 1, 2008) | 0 (~27.5 hr) | |
| 90,000 pmol/g ω-ACTX 20% DMSO/Tween (4:09PM Jul. 1, 2008) | 3 (~27.5 hr) | 1 twitching |
| 9,000 pmol/g ω-ACTX 20% DMSO/Tween (4:22PM Jul. 1, 2008) | 1 (~27 hr) | |
| 900 pmol/g ω-ACTX 20% DMSO/Tween (4:32PM Jul. 1, 2008) | 0 (~27 hr) | |
| −ve 10% DMSO/Tween (5:39PM Jul. 1, 2008) | 1 (~26 hr) | |
| 90,000 pmol/g ω-ACTX 10% DMSO/Tween (4:52PM Jul. 1, 2008) | 3 (~26.5 hr) | 1 twitching |
| −ve 90% Acetone/10%DMSO (5:25PM Jul. 1, 2008) | 1 (~26 hr) | |
| +ve BSA Protein (5:01PM Jul. 1, 2008) | 1 (~26 hr) | |
| 90,0000 pmol/g ω-ACTX (DMSO Stock) 90%Acetone/10% DMSO (5:11PM Jul. 1, 2008) | 3 (~26.5 hr) | 1 twitching |
| 45,0000 pmol/g ω-ACTX (Acetone Stock) 90%Acetone/10% DMSO (5:19PM Jul. 1, 2008) | 7 (~26 hr) | 1 sick |
| −ve untreated (5:40PM Jul. 1, 2008) | 0 (~26 hr) | |

Topical application of ω-ACTX dissolved in Acetone with 10% DMSO was insecticidal to flies (70% mortality at 24 hrs.) while a similar preparation of ω-ACTX dissolved in DMSO then diluted to 10% DMSO in acetone was less insecticidal (~30%). These results are similar to the topical assays in which ω-ACTX dissolved in Acetone with DMSO added to a concentration of 10% killed 90% of houseflies (Jun. 19, 2008) while ω-ACTX dissolved in DMSO and then diluted in Acetone to a concentration of 90,000 pmol/g killed 40% of treated insects. Topical application of ω-ACTX in 10-20% DMSO in water was also insecticidal, but considerably less so than the Acetone/DMSO solution (30% vs. 70%).

Example 2

Topical Assay with Acetone/Methanol/DMSO Using House Fly

Toxin is ω-ACTX-Hv1a:
SPTCIPSGQPCPYNENCCSQSCT-FKENENGNTVKRCD (SEQ. ID. NO. 60)
Synthetic. Molecular weight: 4050 Da. $LD_{50}$ in House-fly: 90.2 pmol/g.
Administration and Application of the Formulation
Insects: House fly (*Musca domestica*) from Benzon research weighing between 12-18 mg (average mass 15 mg); 2 μL micropipette application onto dorsal thorax.
Cabbage Looper (*Trichoplusia ni*) from Benzon research weighing ~30 mg; 2 μL micropipette application to dorsal anterior.
Toxin Dose Calculations: ~90,000 pmol/g ω-ACTX (1000× Injection $LD_{50}$), 0.015 g/fly×90,000 pmol/g=1350 pmol/fly×4050 pg/pmol×1 μg/$10^6$ pg=5.467 μg/insect.

5.467 μg/2 μL application=2.733 μg/μL×150 μL=410.06 μg×1 μL/5 μg=82 μL 5 μg/μL ω-ACTX stock Preparation of Application Solutions.

Mixtures of ω-ACTX in acetone (90%) and DMSO (10%) were prepared according to Table 5 from a stock preparation of 1.5 mg lyophilized ω-ACTX dissolved in 300 μL of acetone to produce a 5 mg/mL solution. ω-ACTX formed a cloudy precipitate when acetone was added which settled out when left on the bench. The preparation was vortexed for ~5 sec to homogenize the precipitate prior to dilution.

Methanol/DMSO—Mixtures of ω-ACTX in methanol (90%) and DMSO (10%) were prepared according to Table 5 from a stock preparation of 2.3 mg lyophilized ω-ACTX dissolved in 460 μL of methanol to produce a mixture with a final peptide concentration of 5 mg/mL. ω-ACTX formed a cloudy precipitate when methanol was added which settled out when left on the bench, in a similar manner to atracotoxin/acetone suspensions. The preparation was vortexed for ~5 sec. to homogenize the precipitate prior to dilution.

TABLE 5

Treatment Preparations.

| Treatment | ω-ACTX | DMSO | Solvent | Total Volume |
|---|---|---|---|---|
| 90,000 pmol/g | 82 μL 5 mg/mL ω-ACTX STOCK in Acetone | 15 μL | 53 μL Acetone | 150 μL |
| −ve | — | 15 μL | 135 μL Acetone | 150 μL |

TABLE 5-continued

Treatment Preparations.

| Treatment | ω-ACTX | DMSO | Solvent | Total Volume |
|---|---|---|---|---|
| 90,000 pmol/g | 82 μL 5 mg/mL ω-ACTX STOCK in Methanol | 15 μL | 53 μL Methanol | 150 μL |
| −ve | — | 15 μL | 135 μL Methanol | 150 μL |

Table 5 treatment preparations are formulations of acetone/methanol/DMSO; order of addition when preparing each formulation was solvent, ω-ACTX stock (where necessary), and finally DMSO.
Administration and Application of the Formulation.

Each treatment formulation described above was applied to a group of ten $CO_2$-anesthetized houseflies. Treatment application consisted of a 2 μL droplet of the respective formulation, pipetted onto the dorsal thoracic body surface of a fly. Each mixture was vortexed immediately prior to each application to ensure suspension of precipitate particles. Following treatment, insects were placed in bins with fresh food and water, allowed to recover, and observed over 24 hours.

Each treatment formulation described above was also applied to a group of ten $2^{nd}$ instar *T. ni*. Treatment application consisted of a 2 μL droplet of the respective formulation, pipetted onto the anterior dorsal body surface. Each mixture was vortexed and immediately prior to each application to ensure suspension of precipitate particles. All treatment mixtures were vortexed immediately prior application to ensure suspension of precipitate particles. Following treatment, insects were placed on fresh media and observed for 24 hrs.

TABLE 6a

Housefly

| Treatment | Dead (18 hrs.) | Dead (24 hrs.) |
|---|---|---|
| 90,000 pmol/g Acetone + DMSO | 4 | 4 |
| −ve Acetone + DMSO | 0 | 0 |
| 90,000 pmol/g Methanol + DMSO | 10 | 10 |
| −ve Methanol + DMSO | 0 | 0 |
| Untreated | 0 | 0 |

TABLE 6b

Cabbage Looper

| Treatment | Dead (18 hr) | Dead (24 hr) |
|---|---|---|
| 45,000 pmol/g Acetone + DMSO | 0 | 0 |
| −ve Acetone + DMSO | 0 | 0 |
| 45,000 pmol/g Methanol + DMSO | 0 | 0 |
| −ve Methanol + DMSO | 0 | 0 |

Table 6a and Table 6b (above) Results of administration of acetone/methanol/DMSO formulations to Housefly and Cabbage Looper.

Topical treatment of houseflies with a high dose of ω-ACTX in methanol with DMSO was insecticidal with 100% mortality at 18 hours post treatment compared to only 40% mortality of houseflies treated with ω-ACTX in acetone.

There was no control mortality in either treatment. There was no difference between ω-ACTX and control treatments of cabbage loopers in terms of insect death, feeding, or behavior. Methanol potentiated the topical activity of ω-ACTX more than acetone in this experiment.

Example 3

Topical Assay with Methanol and Ethanol Using Housefly

Toxin is ω-ACTX-Hv1a (SEQ ID. NO: 60)
SPTCIPSGQPCPYNENCCSQSCTFKENENGNTVKRCD

Synthetic. Molecular weight: 4050 Da $LD_{50}$ in House-fly: 90.2 pmol/g

Administration and Application of the Formulation

Insect: House fly (*Musca domestica*) from Benzon research weighing between 12-20 mg (average mass 16 mg). 2 μL micropipette application onto dorsal thorax.

Toxin Dose Calculations:

90,000 pmol/g ω-ACTX (1000×Injection $LD_{50}$), 0.015 g/fly×90,000 pmol/g=1350 pmol/fly×4050 pg/pmol×1 μg/$10^6$ pg=5.467 μg/insect 5.467 μg/2 μL application=2.733 μg/μL×250 μL=683.43 μg×1 μL/5 μg=136.7 μL 5 μg/μL ω-ACTX stock NOTE: Treatment solutions calculated for flies of an average mass of 15 mg (12-18 mg range); actual average mass of insects used was 16 mg (12-20 mg range). ω-ACTX dose in tables below has been adjusted for this discrepancy.

Preparation of Application Solutions

Methanol—Solutions of ω-ACTX in Methanol were prepared according to Table 7, using a stock preparation of 1.0 mg lyophilized ω-ACTX dissolved in 200 μL of methanol (5 mg/mL solution).

TABLE 7

Methanol Treatment Formulations

| Treatment | ω-ACTX | Methanol | Total Volume |
|---|---|---|---|
| 84,375 pmol/g | 136.68 μL 5 mg/mL ω-ACTX stock | 113.3 μL | 250 μL |
| 16,875 pmol/g | 50 μL 84,375 pmol/g solution | 200 μL | 250 μL |
| 3,375 pmol/g | 50 μL 16,875 pmol/g solution | 200 μL | 250 μL |
| 675 pmol/g | 50 μL 3,375 pmol/g solution | 200 μL | 250 μL |
| 135 pmol/g | 50 μL 675 pmol/g solution | 200 μL | 250 μL |
| −ve | — | 250 μL | 200 μL |

Methanol+DMSO-Solutions of ω-ACTX in methanol were prepared according to Table 8 using a 5 mg/mL stock. The 84,375 pmol/g solution was prepared by diluting the stock mixture into methanol (88.3 μL) before adding DMSO (25 μL) to a final concentration of 10% DMSO. A 10% DMSO in methanol solution was then prepared and aliquoted as described below for the serial dilution series.

TABLE 8

Methanol/DMSO Treatment Solutions

| Treatment | ω-ACTX | DMSO | Methanol | Total Volume |
|---|---|---|---|---|
| 84,375 pmol/g | 136.68 μL 5 mg/mL ω-ACTX STOCK in Methanol | 25 μL (100%) | 88.3 μL | 250 μL |
| 16,875 pmol/g | 50 μL 84,375 pmol/g solution | — | 200 μL (10% DMSO) | 250 μL |
| 3,375 pmol/g | 50 μL 16,875 pmol/g solution | — | 200 μL (10% DMSO) | 250 μL |
| 675 pmol/g | 50 μL 3,375 pmol/g solution | — | 200 μL (10% DMSO) | 250 μL |
| 135 pmol/g | 50 μL 675 pmol/g solution | — | 200 μL (10% DMSO) | 250 μL |
| −ve | — | — | 250 μL (10% DMSO) | 250 μL |

Ethanol+DMSO-Solutions of ω-ACTX in Ethanol were prepared according to Table 9 from a stock preparation of 0.8 mg lyophilized ω-ACTX dissolved in 160 μL of Ethanol to produce a 5 mg/mL solution. The 84,375 pmol/g solution was prepared by diluting the stock solution into ethanol (88.3 μL) before adding DMSO (25 μL) to a final concentration of 10% DMSO. A 10% DMSO/ethanol solution was then prepared and aliquoted as described below for the serial dilution series.

TABLE 9

Ethanol Solution Formulations; order of addition when preparing the 84,375 pmol/g formulation was ethanol, ω-ACTX stock and finally DMSO. A 10% DMSO/Ethanol solution was prepared and aliquoted in labeled tubes, and a 5x serial dilution from the 84,375 pmol/g treatment was carried out.

| Treatment | ω-ACTX | DMSO | Ethanol | Total Volume |
|---|---|---|---|---|
| 84,375 pmol/g | 136.68 μL 5 mg/mL ω-ACTX in Ethanol | 25 μL (100%) | 88.3 μL | 250 μL |
| 16,875 pmol/g | 50 μL 84,375 pmol/g solution | — | 200 μL (10% DMSO) | 250 μL |
| 3,375 pmol/g | 50 μL 16,875 pmol/g solution | — | 200 μL (10% DMSO) | 250 μL |
| 675 pmol/g | 50 μL 3,375 pmol/g solution | — | 200 μL (10% DMSO) | 250 μL |
| 135 pmol/g | 50 μL 675 pmol/g solution | — | 200 μL (10% DMSO) | 250 μL |
| −ve | — | — | 250 μL (10% DMSO) | 250 μL |

Administration and Application of the Formulation

Each treatment formulation described above was applied to a group of ten $CO_2$-anesthetized houseflies. Treatment application consisted of a 2 μL droplet of the respective formulation, pipetted onto the dorsal thoracic body surface of a fly. Each mixture was vortexed immediately prior to each application to ensure suspension of precipitate particles. Following treatment, insects were placed in bins with fresh food and water, allowed to recover, and observed over 60 hours.

Results of Methanol or Ethanol and DMSO Treatments

TABLE 10

Results of treatment with methanol or ethanol and DMSO

| Treatment | Dead (6 hrs.) | Dead (19.5 hrs.) | Dead (24 hrs.) | Dead (50 hrs.) | Dead (60 hrs.) |
|---|---|---|---|---|---|
| −ve control Methanol + DMSO | 0 | 0 | 0 | 0 | 0 |
| 135 pmol/g Methanol + DMSO | 0 | 0 | 0 | 0 | 0 |
| 675 pmol/g Methanol + DMSO | 0 | 0 | 0 | 0 | 0 |
| 3,375 pmol/g Methanol + DMSO | 0 | 0 | 0 | 0 | 0 (1 twch) |
| 16,875 pmol/g Methanol + DMSO | 0 | 0 | 0 (1 twch) | 0 (1 twch) | 0 (1 twch) |
| 84,375 pmol/g Methanol + DMSO | 0 | 3 (3 twch) | 3 (3 twch) | 7 | 7 (1 twch) |
| −ve control Methanol | 0 | 0 | 0 | 0 | 0 |
| 135 pmol/g Methanol | 0 | 0 | 0 | 0 | 0 |
| 675 pmol/g Methanol | 0 | 0 | 0 | 0 | 0 |
| 3,375 pmol/g Methanol | 0 | 0 | 0 | 0 | 0 |
| 16,875 pmol/g Methanol | 0 | 0 | 0 | 1 (1 twch) | 1 |
| 84,375 pmol/g Methanol | 0 | 0 | 0 | 1 | 1 (5 twch) |
| −ve control Ethanol + DMSO | 0 | 0 | 0 | 0 | 0 |
| 135 pmol/g Ethanol + DMSO | 0 | 0 | 0 | 0 | 0 |
| 675 pmol/g Ethanol + DMSO | 1 | 1 | 1 | 1 | 1 |
| 3,375 pmol/g Ethanol + DMSO | 0 | 0 | 0 | 1 | 0 |
| 16,875 pmol/g Ethanol + DMSO | 0 | 3 (1 twch) | 3 (2 twch) | 7 | 7 (1 twch) |
| 84,375 pmol/g Ethanol + DMSO | 2 | 7 | 7 | 7 | 7 (1 twch) |
| Untreated | 0 | 0 | 0 | 0 | 0 |

Topical treatment of houseflies with a high dose (84,375 pmol/g) of ω-ACTX in ethanol with DMSO was insecticidal causing 30% and 70% mortality at 24 and 50 hours post treatment, respectively. The treatments prepared with ethanol were more potent than those prepared with methanol (70% vs. 30% mortality at 24 hrs. for the highest dose, and 30% vs. 0% mortality in 16,875 pmol/g treatment at 24 hrs.). The effect of the highest dose of w-ACTX in methanol with DMSO was not as potent as in the previous assay (3 dead, 3 twitching vs. 10 dead at the highest dose after 24 hrs.).

Methanol/ω-ACTX treatments without DMSO were not insecticidal, suggesting inclusion of an aprotic penetrant or some other type of molecular adjuvant is important to the activity of topical preparations of ω-ACTX.

This experiment shows examples of effective dose ranges of topically applied ω-ACTX diluted in methanol, and what effect the inclusion of DMSO and ethanol has on the insecticidal activity of the formulation in the topical bioassay paradigm used.

Example 4

Topical Assay with the toxin: ω-ACTX-Hv1a

```
                                   (SEQ ID. NO. 55.)
SPTCIPSGQPCPYNENCCSQSCTFKENENGNTVKRCD
```

Molecular weight: 4050. $LD_{50}$ in House-fly: 90.2 pmol/g
Freeze dried aliquots of 1.5 mg toxin prepared from frozen stocks Topical application: groups of ten house flies (*Musca domestica*) from Benzon research, weighing between 12-20 mg (average mass 16 mg), each received a 2 μL micropipette application of toxin precipitate suspended in Ethanol-DMSO on the dorsal thoracic surface of the body.

Preparation of Stock Solutions for Topical and Per Os Treatment:

Stock 1 (vortexed preparation): 1 mL ethanol was added to −1500 μg lyophilized ω-ACTX, and the resulting mixture vortexed vigorously. A 50 μL aliquot of the peptide suspension was then removed for topical application assays and kept on ice for ~2 hrs.; the remainder was divided into two ~475 μL aliquots and then kept on ice for ~2 hrs.

Stock 2 (vortexed and sonicated preparation): 1 mL ethanol was added to ~1500 μg lyophilized ω-ACTX, and the resulting mixture vortexed vigorously, and then sonicated ~10-15 sec., gently ramping up from intensity setting "0" to setting "5" during this period. A 50 μL aliquot of the peptide suspension was then removed for topical application assays and kept on ice for ~2 hrs.; the remainder was divided into two ~475 μL aliquots and then kept on ice for ~2 hrs.

Toxin Dose Calculations:

1.5 μg/μL×2 μL/application×$10^6$ pg/1 μg×1 pmol/4050 pg×1 fly/0.016 g=46,875 pmol/g Topical Application of Toxin Solutions and Results Thereof Stock solutions of ω-ACTX in Ethanol were prepared as described above. Table 11, below, indicates the recipes used to dilute the stock solutions for topical application to houseflies:

TABLE 11

Ethanol/DMSO formulations

| Treatment# (dose) | ω-ACTX | DMSO | 90%EtOH/ 10%DMSO | Total Volume |
|---|---|---|---|---|
| 1-vortexed (46,875 pmol/g) | 50 μL ω-ACTX Stock-1 | 5 μL | — | 55 μL |
| 2-vortexed (9,375 pmol/g) | 10 μL treatment 1 solution | — | 40 μL | 50 μL |
| 3-vortexed + sonicated (46,875 pmol/g) | 50 μL ω-ACTX Stock-2 | 5 μL | — | 55 μL |
| 4- vortexed + sonicated (9,375 pmol/g) | 10 μL treatment 3 solution | — | 40 μL | 50 μL |

Treated flies were kept in containers with ad libitum access to food and water and mortality (and "twitching" behavior, presumably resulting from disruption of physiological norms by action of the toxin) was scored thereafter as indicated in Table 12 below:

TABLE 12

Results of treament with Ethanol/DMSO

| Treatment | N | Dead (7.5 hr) | Dead (14 hr) | Dead (24 hr) | Dead (40 hr) | Dead (48 hr) | Dead (76 hr) |
|---|---|---|---|---|---|---|---|
| 9,000 pmol/g vortexed | 10 | 0 (1 twch) | 1 | 1 | 2 (1 twch) | 2 (2 twch) | 3 (1 twch) |
| 45,000 pmol/g vortexed | 10 | 1 (2 twitch) | 6 | 6 (1 twch) | 8 | 8 | 8 |
| 9,000 pmol/g sonicated | 10 | 2 (2 twch) | 2 (1 twch) | 2 (2 twch) | 3 | 3 | 3 (1 twch) |
| 45,000 pmol/g sonicated | 10 | 5 (2 twch) | 8 | 9 | 9 | 9 | 9 |

This experiment demonstrates that sonicating ω-ACTX suspended in ethanol increases the topical insecticidal activity of the resulting toxin formulation.

The sonication of ethanol-DMSO precipitates of omega-ACTX-Hv1a enhances the insecticidal activity of the omega toxin by increasing the mortality of contact-treated houseflies, up to 24 hrs. post application.

Example 5

Toxins are:

1) ω-ACTX-Hv1a+2:

```
                                          (SEQ ID. NO. 117)
GSSPT CIPSG QPCPY NENCC SQSCT FKENE NGNTV KRCD
```

has three disulfide bridges: 6-20, 13-24 and 19-38.

Molecular weight: 4199. Injection LD50 in Housefly: 77 pmol/g 2) rKappa-ACTX-Hv1c:

GSAIC TGADR PCAAC CPCCP GTSCK AESNG VSYCR KDEP

SEQ ID. NO. 118 has four disulfide bridges: 5-19, 12-24, 15-16, 18-34

Recombinant from pDR2 (pET-32a). Molecular weight: 3912.15

Injection LD50 in Housefly: 389 pmol/g 3) rU-ACTX-Hv1a+2:

GSQYC VPVDQ PCSLN TQPCC DDATC TQERN ENGHT VYYCR A

SEQ ID. NO. 119 has three disulfide bridges: 5-20, 12-25, 19-39

Molecular Weight: 4570.51

Injection LD50 in Housefly: 81.5 pmol/g

Preparation of Mixtures for Topical Treatment:

Recipes for toxin stocks used to formulate treatment mixtures were as follows:

Stock 1: ω-ACTX-Hv1a+2: an aliquot of 1.5 mg freeze dried toxin suspended in 850 μL ethanol and sonicated for 10-15 seconds with gentle ramp from setting "0" to setting "5" on sonicator to create fine particles.

Stock 2: rU-ACTX-Hv1a+2 an aliquot of 1.5 mg freeze dried toxin suspended in 900 μL acetone and sonicated for 10-15 seconds with gentle ramp from setting "0" to setting "5" on sonicator to create fine particles.

Stock 3: rU-ACTX-Hv1a+2: an aliquot of 1.5 mg freeze dried toxin suspended in 900 μL methanol and sonicated for 10-15 seconds with gentle ramp from setting "0" to setting "5" on sonicator to create fine particles.

Stock 4: rKappa-Hv1c+2: an aliquot of 1.5 mg freeze dried toxin suspended in 900 μL acetone and sonicated for 10-15 seconds with gentle ramp from setting "0" to setting "5" on sonicator to create fine particles.

Stock 5: rKappa-Hv1c+2: an aliquot of 1.5 mg freeze dried toxin suspended in 900 μL methanol and sonicated for 10-15 seconds with gentle ramp from setting "0" to setting "5" on sonicator to create fine particles.

Final preparation of mixtures for topical applications was done by mixing stocks with other reagents as listed below:

Control 1—Ethanol+0.05% LI-700-475 μL Ethanol. 25 μL 1% LI-700 in Ethanol

Control 2—Ethanol+0.01% LI-700-495 μL Ethanol. 5 μL 1% LI-700 in Ethanol

Control 3—Ethanol+0.1% MSO®-450 μL Ethanol. 50 μL 1% MSO® in Ethanol

Control 4—Ethanol+0.02% MSO®-490 μL Ethanol. 10 μL 1% MSO® in Ethanol

Treatment 1—ω-ACTX-Hv1a+2 Ethanol Precipitate+10% DMSO+0.05% Silwet-425 μL Stock 1

25 μL 1% Silwet in Ethanol. 50 μL DMSO

Control 5—Ethanol+10% DMSO+0.05% Silwet-425 μL Ethanol

25 μL 1% Silwet in Ethanol. 50 μL DMSO

Treatment 2—rU-ACTX-Hv1a+2 acetone precipitate+10% DMSO−450 μL Stock 2. 50 μL DMSO Treatment 3—rU-ACTX-Hv1a+2 methanol precipitate+10% DMSO−450 μL Stock 3. 50 μL DMSO Treatment 4—rKappa-ACTX-Hv1c acetone precipitate+ 10% DMSO−450 μL Stock 4. 50 μL DMSO Treatment 5—rKappa-ACTX-Hv1c methanol precipitate+ 10% DMSO−450 μL Stock 5. 50 μL DMSO Control 6—Acetone+10% DMSO-450 μL Acetone. 50 μL DMSO Control 7—Methanol+10% DMSO-450 μL methanol. 50 μL DMSO Control 8—Ethanol+10% DMSO-450 μL Ethanol. 50 μL DMSO Administration and Application of the Formulation.

Topical application of 20 μL droplets to the ventral abdomen of houseflies between 12-18 mg with P10 micropipettes, as described in previous examples. After application, flies were provided food and water ad libitum and observed for mortality.

TABLE 13

Results of the mixtures of topical treatments.

| Treatment | 6 hrs. Dead | Twitch/ Morib | 24 hrs. Dead | Twitch/ Morib | 42 hrs. Dead | Twitch/ Morib |
|---|---|---|---|---|---|---|
| LI-700 (n = 10) | | | | | | |
| Control 1 - Ethanol + 0.05% LI-700 | 0 | 4/0 | 0 | 3/1 | 1 | 1/1 |
| Control 2 - Ethanol + 0.01% LI-700 | 0 | 6/0 | 1 | 4/1 | 1 | 4/2 |
| MSO (n = 10) | | | | | | |
| Control 3 - Ethanol + 0.1% MSO ® | 2 | 4/1 | 2 | 4/0 | 3 | 2/1 |
| Control 4 - Ethanol + 0.02% MSO ® | 0 | 7/0 | 1 | 5/0 | 4 | 1/1 |
| Silwet (n = 10, ~45,000 pmol/g) | | | | | | |
| Treatment 1-ω-ACTX-Hv1a + 2 precipitate + ~10% DMSO + 0.05% Silwet | 2 | 3/0 | 7 | 1/2 | 10 | 0/0 |
| Control 5 - Ethanol + ~10% DMSO + 0.05% Silwet | 1 | 0/0 | 1 | 0/0 | 2 | 0/0 |
| Acetone/Methanol Precipitation (n = 10, ~45,000 pmol/g) | | | | | | |
| Treatment 2 -rU-ACTX-Hv1a + 2 acetone precipitate + 10% DMSO | 0 | 0/0 | 1 | 2/0 | 5 | 2/0 |
| Treatment 3 - rU-ACTX-Hv1a + 2 methanol precipitate + 10% DMSO | 0 | 0/0 | 2 | 1/0 | 5 | 2/0 |
| Treatment 4 - rKappa-ACTX-Hv1c + 2 acetone precipitate* + 10% DMSO | 0 | 1/0 | 0 | 1/0 | 5 | 3/0 |
| Treatment 5 - rKappa-ACTX-Hv1c + 2 methanol precipitate* + 10% DMSO | 0 | 1/0 | 1 | 1/0 | 4 | 0/0 |
| Control 6 - Acetone + 10% DMSO | 0 | 0/0 | 1 | 0/0 | 2 | 0/0 |
| Control 7 - Methanol + 10% DMSO | 0 | 0/0 | 0 | 0/0 | 1 | 0/0 |
| Control 8 - Ethanol + 10% DMSO | 0 | 0/0 | 0 | 0/0 | 0 | 0/0 |

Concentrations of LI-700 down to 0.01% resulted in considerable disruption in the behavior of the treated flies, and possibly some mortality as well. Concentrations of MSO® down to 0.02% resulted in considerable disruption in the behavior of the treated flies, and considerable (i.e., 30-40%) mortality as well. Silwet, 0.05%, may slightly potentiate the topical insecticidal activity of omega-toxin/ethanol/dmso suspensions in this experimental paradigm. Based on results presented here and other undisclosed studies potentiation would be in the range of 15-20%.

Topically applied formulations of the hybrid and kappa avacotoxin-1s are insecticidal when 90% acetone or 90% methanol is substituted for 90% ethanol. The acetone and methanol formulations of the hybrid toxin may be slightly less insecticidal than the previously tested ethanol formulation. We believe that acetone and methanol formulations result in equivalent or slightly higher levels of insecticidal activity when compared to ethanol formulations of kappa toxin.

Example 6

Toxin to Apply Topically is ω-ACTX-Hv1a

```
(SEQ ID. NO. 60)
SPTCIPSGQPCPYNENCCSQSCTFKENENGNTVKRCD
```

having a Molecular weight: 4050. LD50 in House-fly: 90.2 pmol/g.

Freeze dried aliquots of 1.5 mg toxin prepared from frozen stocks.

Administration and Application of the Formulation

Topical application: groups of ten house flies (*Musca domestica*) from Benzon research, weighing between 12-20 mg (average mass 16 mg), each received a 2 μL micropipette application of toxin precipitate suspended in Ethanol-DMSO on the dorsal thoracic surface of the body.

Preparation of Stock Solutions for Topical Treatment:

Stock 1 (vortexed and sonicated Ethanol preparation): 0.9 mL ethanol was added to ~1500 μg lyophilized ω-ACTX, and the resulting mixture vortexed vigorously, and then sonicated ~10-15 sec., gently ramping up from intensity setting "0" to setting "5" during this period. 0.1 mL DMSO was then added to the toxin suspension, the resulting mixture was vortexed, and a 100 μL aliquot of the alcohol-DMSO-peptide suspension was then removed for topical application assays and kept on ice for ~2 hrs.

Stock 2 (vortexed and sonicated 1-Propanol preparation): 0.9 mL 1-propanol was added to ~1500 μg lyophilized ω-ACTX, and the resulting mixture vortexed vigorously, and then sonicated ~10-15 sec., gently ramping up from intensity setting "0" to setting "5" during this period. 0.1 mL DMSO was then added to the toxin suspension, the resulting mixture was vortexed, and a 100 μL aliquot of the alcohol-DMSO-peptide suspension was then removed for topical application assays and kept on ice for ~2 hrs.

Stock 3 (vortexed and sonicated 2-Propanol preparation): 0.9 mL 2-propanol was added to ~1500 μg lyophilized ω-ACTX, and the resulting mixture vortexed vigorously, and then sonicated ~10-15 sec., gently ramping up from intensity setting "0" to setting "5" during this period. 0.1 mL DMSO was then added to the toxin suspension, the resulting mixture was vortexed, and a 100 μL aliquot of the alcohol-DMSO-peptide suspension was then removed for topical application assays and kept on ice for ~2 hrs.

Stock 4 (vortexed and sonicated 2-Butanol preparation): 0.9 mL 2-butanol was added to ~1500 μg lyophilized ω-ACTX, and the resulting mixture vortexed vigorously, and then sonicated ~10-15 sec., gently ramping up from intensity setting "0" to setting "5" during this period. 0.1 mL DMSO was then added to the toxin suspension, the resulting mixture was vortexed, and a 100 μL aliquot of the alcohol-DMSO-peptide suspension was then removed for topical application assays and kept on ice for ~2 hrs.

Note that each stock was made to a concentration such that a 2 μL application of the stock to the body surface of a ~16 mg housefly would result in a toxin dose of ~45,000 pmol/g. Hence, in some cases described below, one of the four stocks described above was topically applied full-strength to houseflies, but in other cases, five-fold serial dilutions were performed (using the stocks and the corresponding 90% alcohol-10% DMSO solution) in order to obtain a solution that could be used to deliver a lower toxin dose in a 2 μL volume. Negative control procedures (indicated as "−ve" in the table below) comprised house flies treated with 2 μL dorsal throracic applications of solutions of the alcohols in question (diluted to 90% v/v with DMSO).

Topical Application of Toxin Solutions and Results Thereof:

Stock solutions of ω-ACTX in various alcohols were prepared as described above. Table 14 below indicates the stock formulations and dosing used for topical application to houseflies and the observed mortality for the corresponding groups of flies:

TABLE 14

Results of topical application of toxin solutions When normalized for mortality observed in negative control groups (dosed with the corresponding alcohol-DMSO solution), ethanol precipitates of omega toxin appear to have insecticidal activity as high or higher than any other toxin-alcohol precipitate tested in this series of experiments.

| Treatment | # of Flies Treated | Dead (~16 hr) | Dead (24 hr) | Dead (52 hr) | Dead (64 hr) |
|---|---|---|---|---|---|
| 1-Propanol −ve | 10 | 0 | 0 | 0 | 0 |
| 1-Propanol 9,000 pmol/g | 10 | 0 | 0 | 1 | 1 |
| 1-Propanol 45,000 pmol/g | 10 | 1 (1 twitch) | 2 (1 twitch) | 2 (1 twitch) | 2 (1 twitch) |
| 2-Propanol −ve | 10 | 1 (2 twitch) | 2 (1 twitch) | 3 | 3 |
| 2-Propanol 9,000 pmol/g | 10 | 3 (2 twitch) | 4 (1 twitch) | 4 | 4 |
| 2-Propanol 45,000 pmol/g | 10 | 5 (3 twitch) | 5 (3 twitch) | 8 | 8 |
| 2-Butanol −ve | 10 | 5 | 7 | 7 | 7 |
| 2-Butanol 9,000 pmol/g | 10 | 6 | 6 (1 twitch) | 6 (1 twitch) | 7 (2 twitch) |
| Ethanol −ve | 7 | 0 | 0 | 0 | 0 |
| Ethanol 1,800 pmol/g | 10 | 0 | 1 | 1 | 1 |
| Ethanol 9,000 pmol/g | 10 | 2 | 2 | 2 | 2 (2 twitch) |
| 1-Octanol −ve | 10 | 10 | 10 | 10 | 10 |

90% octanol-10% DMSO, 90% 2-butanol-10% DMSO, and 90% 2-propanol-10% DMSO appear to cause unacceptable levels of background mortality; the latter could presumably mask mortality due to target site action of omega toxin in treated houseflies. 90% 1-propanol-10% DMSO does not appear to cause unacceptable levels of background mortality, but it also does not appear to potentiate target site activity of applied toxin as well as 90% ethanol-10% DMSO.

Example 7

Toxin to Apply Topically

ω-ACTX-Hv1a+2: GSSPTCIPSGQPCPYNENCCSQSCT-FKENENGNTVKRCD (SEQ ID. NO. 117). Molecular weight: 4196

Freeze dried aliquots of 1.5 mg toxin prepared from frozen stocks

Treatment Mixture Preparation

All treatments were made to 1.5 μg/μL final concentration of ω-ACTX-Hv1a+2. As previously, ethanol was added to −1500 μg samples of lyophilized ω-ACTX-Hv1a+2, the resulting mixture was vortexed vigorously, then sonicated ~10-15 sec., gently ramping up from intensity setting "0" to setting "5" during this period. Additional ingredients such as DMSO, MSO®, water, and Tween 20 detergent were added following sonication, and the resulting mixtures were vortexed vigorously prior to topical application in order to ensure even mixing of ingredients. Assuming average fly mass of 16 mg (12-20 mg cohort) dosing is calculated as follows:

3 μg/insect×1 μmol/4196 μg×$10^6$ pmol/1 μmol×1 insect/0.016 g=44,685 pmol/g dose Recipes for toxin stocks used to formulate treatment mixtures were as follows:

Stock 1—1.5 mg lyophilized ω-ACTX-Hv1a+2 dissolved in 500 μL ethanol, vortexed and sonicated.

Stock 2—1.5 mg lyophilized ω-ACTX-Hv1a+2 dissolved in 150 μL sterile water (10 mg/mL).

Topical Assays using ω-ACTX-Hv1a+2 with DMSO:

Recipes for treatment mixtures were as follows:

45,000 pmol/g ω-ACTX-Hv1a+2 90% Ethanol/10% DMSO solution (+-ve control)−50 μL Stock 1, 40 μL ethanol, 10 μL DMSO.

90% Water/10% DMSO/0.1% Tween 20 (−ve control)−7.5 μL Stock 2, 82.5 μL sterile water, 10 μL DMSO. 1 μL 10% Tween 20.

45,000 pmol/g ω-ACTX-Hv1a+2 80% Ethanol/10% Water/10% DMSO−50 μL Stock 1, 30 μL ethanol, 10 μL sterile water, 10 μL DMSO.

45,000 pmol/g ω-ACTX-Hv1a+2 70% Ethanol/20% Water/10% DMSO−50 μL Stock 1, 20 μL ethanol, 20 μL sterile water, 10 μL DMSO.

45,000 pmol/g ω-ACTX-Hv1a+2 60% Ethanol/30% Water/10% DMSO−50 μL Stock 1, 10 μL ethanol, 30 μL sterile water, 10 μL DMSO.

45,000 pmol/g ω-ACTX-Hv1a+2 50% Ethanol/30% Water/10% DMSO−50 μL Stock 1, 40 μL sterile water, 10 μL DMSO.

For Topical Assay using ω-ACTX-Hv1a+2 with MSO® Surfactant:

5% MSO® (−ve control)−95 μL Ethanol, 5 μL MSO® Concentrate.

1.25% MSO® (−ve control)−98.75 μL Ethanol, 1.25 μL MSO® Concentrate.

45,000 pmol/g ω-ACTX-Hv1a+2 5% MSO®−50 μL Stock 1, 45 μL Ethanol, 5 μL MSO® Concentrate.

45,000 pmol/g ω-ACTX-Hv1a+2 2.5% MSO®−25 μL Stock 1, 23.75 μL Ethanol, 1.25 MSO® Concentrate.

45,000 pmol/g ω-ACTX-Hv1a+2 1.25% MSO®−25 μL Stock 1, 24.37 μL Ethanol, 0.625 μL MSO® Concentrate All treatment mixtures were kept on ice for ~1 hr. prior to administration and application.

Administration and Application of the Formulation.

2 μL samples of each treatment mixture were spotted onto the dorsal thorax of individual houseflies (10 houseflies treated per mixture). A second group of ten flies were each treated with 2 μL samples of the 45,000 pmol/g ω-ACTX-Hv1a+2 in 90% Ethanol/10% DMSO but with the treatment applied to the ventral abdominal surface of the flies rather than the dorsal thoracic surface. After application, flies were kept in plastic containers wells with ad libitum access to food (1:1 mixture of dry powdered milk and table sugar) and water (presented in soaked cotton balls) and observed every 8-24 hrs. for two days.

Results of Topical Application of ω-ACTX-Hv1a+2

Post-application mortality (and "twitching" and "moribund" behavior, both presumably resulting from disruption of physiological norms by action of the toxin) is summarized in Table 15, below.

TABLE 15

Results of topical assays of DMSO, ethanol and MSO ® preparations of ω-ACTX-Hv1a + 2, administered topically.

| Treatment | N | Dead (4 hr) | Dead (14 hr) | Dead (22 hr) | Dead (38 hr) | Dead (48 hr) |
|---|---|---|---|---|---|---|
| -ve 90EtOH/10DMSO | 10 | 0 | 0 | 0 | 0 | 0 |
| 45,000 pmol/g 90EtOH/10DMSO | 10 | 1 | 2 | 3 | 5 | 5 (1 twch) |
| 45,0000 pmol/g 80EtOH/10H2O/10DMSO | 10 | 0 | 1 | 2 (1 twch) | 4 | 4 (1 twch) |
| 45,0000 pmol/g 70EtOH/20H2O/10DMSO | 10 | 0 | 0 | 0 | 0 | 0 |
| 45,0000 pmol/g 60EtOH/30H2O/10DMSO | 10 | 0 | 0 | 0 | 0 | 0 |
| 45,0000 pmol/g 50EtOH/40H2O/10DMSO | 10 | 0 | 0 | 0 | 1 | 1 |
| 45,000 pmol/g 90H2O/10DMSO | 10 | 0 | 1 | 0 | 1 | 1 (3 twch) |
| -ve 5% MSO ® | 10 | 0 | 0 | 0 | 0 | 1 |
| -ve 1.25% MSO ® | 10 | 0 | 0 (1 morb) | 1 | 1 (1 morb) | 1 |
| 45,000 pmol/g 5% MSO ® | 10 | 2 (1 twch) | 4 (1 morb) | 4 | 4 (1 morb) | 5 (1 twch) |
| 45,000 pmol/g 2.5% MSO ® | 10 | 0 | 3 | 4 | 4 (1 twch) | 5 (1 twch) |
| 45,000 pmol/g 1.25% MSO ® | 10 | 1 | 1 | 1 | 5 (1 twch) | 6 (1 twch) |
| 45,000 pmol/g 90EtOH/10DMSO TUMMY | 10 | 0 | 1 (3 twch) | 5 (1 twch) | 5 (1 twch) | 7 |

Numbers above are described below.

Number 1—addition of 10% water to precipitates of omega toxin in ethanol/DMSO solutions appears to reduce topical insecticidal activity of the precipitate under the conditions tested above.

Number 2—addition of 20%, 30%, and 40% water to precipitates of omega toxin in ethanol/DMSO solutions appears to completely eliminate topical insecticidal activity of the precipitate under the conditions tested above.

Number 3—solvation/dilution of toxin in 90% water/10% DMSO results in a solution with no insecticidal activity under the conditions tested above.

Number 4—replacement of 10% DMSO with either 1.25% MSO®, 2.5% MSO®, or 5% MSO® apparently results in mixtures with significant insecticidal activity under the conditions tested above.

Number 5—under experimental conditions used above, ventral abdominal application of the precipitate (of omega toxin in 90% ethanol/10% DMSO) appears to induce insect mortality with speed and effectiveness similar to, if not greater than, the induction of mortality by dorsal thoracic application of the same precipitate mixture. Since ventral abdominal application can be executed roughly twice as quickly as dorsal thoracic application, this points to a significant technical improvement for future topical application bioassays.

Further Examples of Toxic Peptides and the Sequence Listing.

The toxic insect peptides refers to peptides that are not from toxic insects, but that are toxic to insects. Their source need not be insects. In the sequence listing of this application a wide range of suitable toxic insect peptides are provided. This small selection of about 174 peptides includes representative peptides from spiders, scorpions and plants. Sequences 1-140 are from funnel web spiders, sequences 141 to 171 are from scoprions and sequences 172 to 174 are from plants. The sequence listing includes peptide examples where the source is *Oldenlandia affinis* which is known to produce a cyclic peptide referred to at a "Kalata" type peptide. The *Oldenlandia* plant family is known to produce peptides having insecticidal activity. Other insecticidal peptides from plants are known. Numerous venomus spider peptides, which are discussed throughout this application are also provided.

We claim:

1. A hybrid peptide toxic to insects, comprising SEQ ID NO: 117.

2. A hybrid peptide toxic to insects, comprising SEQ ID NO: 119.

3. A hybrid peptide toxic to insects, comprising SEQ ID NO: 118.

* * * * *